(12) United States Patent
Motterlini et al.

(10) Patent No.: US 10,519,179 B2
(45) Date of Patent: Dec. 31, 2019

(54) HIGHLY EFFICIENT NRF2 ACTIVATORS-CO-RELEASING MOLECULE HYBRIDS, THEIR USE IN THE TREATMENT OF INFLAMMATORY OR CARDIOVASCULAR DISEASES AND THEIR PROCESS OF PREPARATION

(71) Applicants: Centre National de la Recherche Scientifique, Paris (FR); Universite Paris est Creteil val de Marne, Creteil (FR); Institut National de la Sante et de la Recherche Medicale, Paris (FR)

(72) Inventors: Roberto Motterlini, Paris (FR); Roberta Foresti, Paris (FR); Anthony Ollivier, Vitry sur Seine (FR); Michael Rivard, Creteil (FR); Thierry Martens, La Queue en Brie (FR)

(73) Assignees: CENTRE NATIONAL DE LA RECHERCHE SCIENTIFIQUE, Paris (FR); UNIVERSITE PARIS EST CRETEIL VAL DE MARNE, Creteil (FR); INSTITUTE NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 0 days.

(21) Appl. No.: 15/762,488

(22) PCT Filed: Sep. 23, 2016

(86) PCT No.: PCT/EP2016/072696
§ 371 (c)(1),
(2) Date: Mar. 22, 2018

(87) PCT Pub. No.: WO2017/050970
PCT Pub. Date: Mar. 30, 2017

(65) Prior Publication Data
US 2018/0258121 A1 Sep. 13, 2018

(30) Foreign Application Priority Data
Sep. 24, 2015 (EP) .................... 15020173

(51) Int. Cl.
*A61P 9/00* (2006.01)
*A61P 29/00* (2006.01)
(Continued)

(52) U.S. Cl.
CPC .............. *C07F 15/06* (2013.01); *A61P 9/00* (2018.01); *A61P 29/00* (2018.01); *C07F 13/00* (2013.01)

(58) Field of Classification Search
CPC .. A61P 9/00; A61P 29/00; C07F 15/06; C07F 13/00
See application file for complete search history.

(56) References Cited

FOREIGN PATENT DOCUMENTS

WO 2012076696 A1 6/2012

OTHER PUBLICATIONS

"Design and Synthesis of New Hybrid Molecules That Activate the Transcription Factor Nrf2 and Simultaneously Release Carbon Monoxide," Wilson, et al., Chemistry—A European Journal, vol. 20, No. 45, Nov. 3, 2014.
(Continued)

*Primary Examiner* — Brenda L Coleman
(74) *Attorney, Agent, or Firm* — Steven M. Shape; Dennemeyer & Associates, LLC

(57) ABSTRACT

The present invention relates to highly efficient Nrf2 activators-CO-releasing molecules of formula (I) and (II) capable of increasing HO-1 protein expression and simultaneously releasing CO, their synthesis and their use in therapeutic applications, in particular their use in the treatment of inflammatory or cardiovascular diseases, wherein CORM represents a carbonyl metal complex chosen from among: $Mn(CO)_5$, formula (III), (IV), (V), (VI), (VII), (VIII) and (IX).

(Continued)

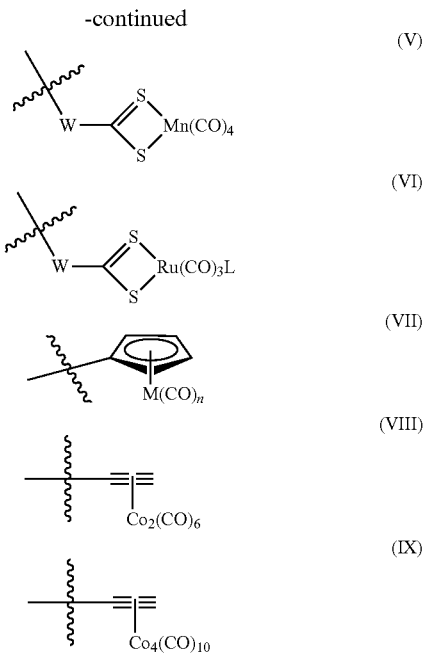

13 Claims, 10 Drawing Sheets

(51) Int. Cl.
C07F 15/06 (2006.01)
C07F 13/00 (2006.01)

(56) References Cited

OTHER PUBLICATIONS

"Small molecule activators of the Nrf2-HO-1 antioxidant axis modulate heme metabolism and inflammation in Bv2 microglia cells," Foresti, et al., Pharmacological Research 76, 132-148, Jul. 2013.
International Search Report issued by the European Patent Office in connection with PCT/EP2016/072696 dated Nov. 7, 2016.
Min Long, et al, "An Essential Role of NRF2 in Diabetic Healing", vol. 65, Mar. 2016, DOI: 10.2337/db15-0564.
Akira Uruno, et al, "The Keap1-Nrf2 System Prevents Onset of Diabetes Mellitus", 2013, INSERM.
Ana I. Rojo, et al, "NRF2 deficiency replicates transcriptomic changes in Alzheimer's patients and worsens APP and TAU pathology", Jul. 3, 2017, Redox Biology 13, Published by Elsevier B.V.
Isabel Lastres-Becker, et al, "Repurposing the NRF2 Activator Dimethyl Fumarate as Therapy Against Synucleinopathy in Parkinson's Disease", Antioxidants & Redox Signaling vol. 25, No. 2, 2016, Mary Ann Liebert, Inc., DOI: 10.1089/ars.2015.6549.
Fabienne Tamion, et al, "Induction of Heme-oxygenase-1 Prevents the Systemic Responses to Hemorrhagic Shock", Am J Respir Crit Care Med vol. 164. pp. 1933-1938, 2001, DOI: 10.1164/rccm2010074.
T. Draheim, et al, "Activation of the Astrocytic Nrf2/ARE System Ameliorates the Formation of Demyelinating Lesions in a Multiple Sclerosis Animal Model", Sep. 19, 2016, Wiley Periodicals, Inc., DOI: 10.1002/glia.23058.
John G. Yonchuk, et al, Characterization of the Potent, Selective Nrf2 Activator, PSTC, in Cellular and In Vivo Models of Pulmonary Oxidative Stress, JPET Fast Forward. Published on Aug. 8, 2017 as DOI: 10.1124/jpet.117.241794.
Yukio Ishii, et al, "Transcription Factor Nrf2 Plays a Pivotal Role in Protection against Elastase-Induced Pulmonary Inflammation and Emphysema", The Journal of Immunology, 2005, 175:6968-6975, doi: 10.4049/jimmunol.175.10.6968.
Libor Vitek, et al, "Antiproliferative effects of carbon monoxide on pancreatic cancer", Digestive and Liver Disease 46 (2014) 369-375.
Magdalena Tertil, et al, "Nrf2-heme oxygenase-1 axis in mucoepidermoid carcinoma of the lung: Antitumoral effects associated with down-regulation of matrix metalloproteinases" Free Radical Biology and Medicine 89 (2015) 147-157.
Roberto Motterlini, et al, "Heme Oxygenase-1-Derived Carbon Monoxide Contributes to the Suppression of Acute Hypertensive Responses In Vivo", pp. 568-577, Sep. 7, 1998, American Heart Association, Inc.
Helen Christou, et al, "Prevention of Hypoxia-Induced Pulmonary Hypertension by Enhancement of Endogenous Heme Oxygenase-1 in the Rat", Jun. 23, 2000, Circ Res. 2000, 86:1224-1229, American Heart Association, Inc.
Shaw-Fang Yet, et al, "Cardiac-Specific Expression of Heme Oxygenase-1 Protects Against Ischemia and Reperfusion Injury in Transgenic Mice", Jul. 20, 2001, Circulation Research. 2001;89:168-173.
A Nakao, et al, "Immunomodulatory effects of inhaled carbon monoxide on rat syngeneic small bowel graft motility", Gut 2003, 52:1278-1285.
Refaat A.F. Hegazi, et al, "Carbon monoxide ameliorates chronic murine colitis through a heme oxygenase 1-dependent pathway", vol. 202, No. 12, Dec. 19, 2005 1703-1713, The Journal of Experimental Medicine.
Xiaoli Liu, et al, "Heme oxygenase-1 (HO-1) inhibits postmyocardial infarct remodeling and restores ventricular function", vol. 20, 207-216, Feb. 2006, The FASEB Journal.
Hideo Kobayashi, et al, "Regulatory Role of Heme Oxygenase 1 in Inflammation of Rheumatoid Arthritis", Arthritis & Rheumatism vol. 54, No. 4, Apr. 2006, pp. 1132-1142, DOI 10.1002/art.21754, American College of Rheumatology.
Maria Jose Alcaraz, et al, "Carbon Monoxide-Releasing Molecules: A Pharmacological Expedient to Counteract Inflammation", Current Pharmaceutical Design, 2008, 14, 465-472, Bentham Science Publishers Ltd.
M L Ferrandiz, et al, "Treatment with a CO-releasing molecule (CORM-3) reduces joint inflammation and erosion in murine collagen-induced arthritis", Ann Rheum Dis 2008, 67, 1211-1217, originally published online Dec. 6, 2007, doi:10.1136/ard.2007.082412.
O De Backer, et al, "Water-soluble CO-releasing molecules reduce the development of postoperative ileus via modulation of MAPK/HO-1 signalling and reduction of oxidative stress", Gut 2009, 58, 347-356; originally published online Nov. 20, 2008; doi:10.1136/gut.2008.155481.
Steve Lancel, et al, "Carbon Monoxide Rescues Mice from Lethal Sepsis by Supporting Mitochondrial Energetic Metabolism and Activating Mitochondrial Biogenesis", The Journal of Pharmacology and Experimental Therapeutics 2009, vol. 329, No. 2, 641-648, 148049/3458612.
Anna Grochot-Przeczek, et al, "Heme Oxygenase-1 Accelerates Cutaneous Wound Healing in Mice", Jun. 2009, vol. 4, Issue 6, pp. 1-16, e5803, PLoS ONE.
Joseph Fomusi Ndisang, et al, "Upregulation of the heme oxygenase system ameliorates postprandial and fasting hyperglycemia in type 2 diabetes", Am J Physiol Endocrinol Metab 296: E1029-E1041, 2009. First published Feb. 10, 2008; the American Physiological Society, doi:10.1152/ajpendo.90241.2008.
Atsunori Nakao, et al, "Low-dose carbon monoxide inhibits progressive chronic allograft nephropathy and restores renal allograft function", Am J Physiol Renal Physiol 297: F19-F26, 2009. First published Apr. 15, 2009; the American Physiological Society, doi:10.1152/ajprenal.90728.2008.
Joan D. Beckman, et al, "Inhaled carbon monoxide reduces leukocytosis in a murine model of sickle cell disease", Am J Physiol Heart Circ Physiol. Oct. 2009; 297(4): H1243-H1253, PMCID: PMC2770753.
Bing Wang, et al, "Carbon Monoxide-Activated Nrf2 Pathway Leads to Protection Against Permanent Focal cerebral Ischemia",

(56) References Cited

OTHER PUBLICATIONS

Stroke 2011, 42, 2605-2610: originally published online Aug. 18, 2011, the American Heart Association, doi: 10.1161/STROKEAHA. 110.607101.
Houman Ashrafian, et al, "Fumarate Is Cardioprotective via Activation of the Nrf2 Antioxidant Pathway", Cell Metabolism 15, 361-371, Mar. 7, 2012, Elsevier Inc.
Steve Lancel, et al, "Carbon Monoxide Improves Cardiac Function and Mitochondrial Population Quality in a Mouse Model of Metabolic Syndrome", Aug. 2012, vol. 7, Issue 8, pp. 1-11, e41836, PLoS ONE.
Arnau Hervera, et al, "Carbon Monoxide Reduces Neuropathic Pain and Spinal Microglial Activation by Inhibiting Nitric Oxide Synthesis in Mice", Aug. 2012, vol. 7, Issue 8, pp. 1-10, e43693, PLOS ONE.
Kamran Ghoreschi, et al, "Fumarates improve psoriasis and multiple sclerosis by inducing type II dendritic cells", J. Exp. Med. vol. 208, No. 11, 2291-2303, The Rockefeller University Press, 2011.
Rabea Hinkel, DVM, et al, "Heme Oxygenase-1 Gene Therapy Provides Cardioprotection Via Control of Post-Ischemic Inflammation an Experimental Study in a Pre-Clinical Pig Model", Journal of the American College of Cardiology, vol. 66, No. 2, pp. 154-165, Jul. 14, 2015, The American College of Cardiology Foundation, Published by Elsevier Inc., ISSN 0735-1097.
Barbara Wegiel, et al, "Carbon Monoxide Expedites Metabolic Exhaustion to Inhibit Tumor Growth", Cancer Research, 73(23) Dec. 1, 2013, pp. 7009-7021, American Association for Cancer Research Journals.

A

B

HIGHLY EFFICIENT NRF2 ACTIVATORS-CO-RELEASING MOLECULE HYBRIDS, THEIR USE IN THE TREATMENT OF INFLAMMATORY OR CARDIOVASCULAR DISEASES AND THEIR PROCESS OF PREPARATION

CROSS-REFERENCE TO RELATED APPLICATIONS

This is a 35 U.S.C. 371 National Stage Patent Application of International Application No. PCT/EP2016/072696, filed Sep. 23, 2016, which claims priority to European application 15020173.9, filed Sep. 24, 2015, each of which is hereby incorporated by reference in its entirety.

FIELD OF THE INVENTION

The present invention relates to highly efficient hybrid Nrf2 activators-CO-releasing molecules capable of increasing HO-1 protein expression and CO release, their synthesis and their use in therapeutic applications, in particular their use in the treatment of inflammatory and cardiovascular diseases.

BACKGROUND ART

The HO-1/CO system is a significant part of the defense against the damage inflicted by a variety of stress conditions mediated by heavy metals, reactive oxygen species, lipopolysaccharide (LPS) and other inflammatory processes, thereby playing a pivotal role in the regulation of the cytoprotective and anti-inflammatory responses. CO gas administered at low doses (250 ppm) for restricted period of times has been shown to restore many of the beneficial effects of HO-1 in models of cardiovascular dysfunction, pulmonary hypertension, and inflammatory conditions such as sepsis and inflammatory bowel disease.

Because of the interest in HO-1/CO therapeutic potential, compounds that liberate controlled amounts of CO (CO-releasing molecules, CO-RMs) to biological systems have been developed and demonstrated to exert a wide array of pharmacological effects related to CO release. The vast majority of pharmacologically active CO-RMs described in the literature are metal carbonyls containing either Ru, Fe, Mn, Co and Mo.

The transcription factor Nrf2 is a crucial initiator of the cellular stress response as it co-ordinates the expression of several antioxidant and detoxification genes that repair damage and restore cellular homeostasis. As part of this inducible response, heme oxygenase-1 (HO-1) plays a prominent role by utilizing heme to produce CO, biliverdin/bilirubin and iron, important signaling and protective molecules against oxidative stress and inflammation.

The list of Nrf2/HO-1 activators has now grown to include several hundred compounds. Because of their mechanism of action, Nrf2/HO-1 activators require time to mount the cellular stress response, resulting in a delayed, albeit essential, beneficial effect.

WO 2012/076696 discloses curcumin derivatives bound to a CO-releasing molecule. The inventors of the present invention have however shown that these molecules do not release carbon monoxide. This lack of CO-release results in molecules that do not exhibit the wide array of beneficial therapeutic effects related to the activation of HO-1 by CO.

The synthesis and preliminary biological characterization of two fumarate-CORM molecules exhibiting the dual ability to activate the Nrf2/HO-1 cytoprotective pathway and to release controlled amounts of CO have been reported (Wilson et al. Chem. Eur. J. 2014, 20, 14698-14704).

Antioxidant and detoxification genes transcribed after Nrf2 activation include those involved in the synthesis of glutathione, the most important and abundant cellular thiol protecting against oxidative stress. As proposed by Satoh and Lipton (Sato T et al. Free Rad. Biol. Med. 2013, 65, 645-657), drugs developed as Nrf2 activators should be evaluated for their two opposing actions: cytoprotective versus cytotoxic effects. The cytoprotective effects are due to the extent of activation of Nrf2-dependent genes while cytotoxicity involves glutathione (GSH) depletion. Thus, in terms of tolerability, it is desirable to produce compounds that cause a strong Nrf2-dependent response without markedly depleting GSH content, and with a low cytotoxicity.

Hence, there is a need to find enhanced hybrids containing an Nrf2 inducer bound to a CO-releasing molecule, that will provide greater tissue protection by first limiting damage through CO delivery and subsequently promoting the endogenous up-regulation of Nrf2-dependent defensive genes and proteins, a process that takes several hours due to transcription and translation processes.

BRIEF SUMMARY OF THE INVENTION

Inventors of the present invention have discovered two families of hybrid molecules comprising a Nrf2 activator moiety and a CO-releasing molecule (CORM) that are capable of rapidly liberating CO and activating the Nrf2/HO-1 pathway, resulting in a dual activation of the inflammatory defenses in cells and an improved therapeutic efficacy compared to several other compounds. Those hybrid molecules can furthermore up-regulate tissue HO-1 and deliver CO in vivo.

Moreover, those hybrids further display a faster CO release and a better anti-inflammatory action compared to known hybrids, a low cytotoxic profile, a significantly higher Nrf2 and HO-1 activation compared to other hybrids and have a low impact on GSH depletion.

Thus, those compounds show an overall enhanced efficacy.

A first object of the invention is a compound of the following general formula (I):

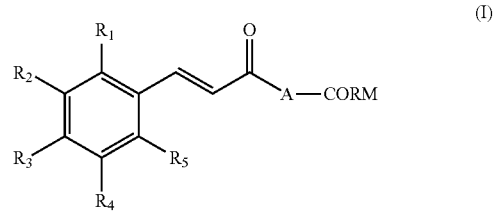

(I)

wherein:
A represents:
  a single bond, or
  -Q-Z-, where:
    Q represents O, S or $NR_6$, where $R_6$ represents H, $(C_1$-$C_6)$alkyl, aryl, heteroaryl, $(C_1$-$C_6)$alkyl-aryl, $(C_1$-$C_6)$alkyl-heteroaryl, $(C_1$-$C_6)$alkyl-$(C_3$-$C_8)$heterocyclyl, —$(C_3$-$C_{14})$cycloalkyl, or $R_6$ and Z are connected to form a $(C_3$-$C_8)$heterocyclyl,
    Z represents —$(C_1$-$C_6)$alkyl-, —$(C_2$-$C_6)$alkenyl-, -aryl-, -heteroaryl-, —$(C_2$-$C_6)$alkynyl-, —$(C_3$-$C_8)$ heterocyclyl-, —($C_3$-$C_{14}$)cycloalkyl, —($C_1$-$C_6$)alkyl-$R_7$—($C_1$-$C_6$)alkyl-, —($C_2$-$C_6$)alkenyl-$R_7$—($C_1$-$C_6$)alkyl-, —($C_1$-$C_6$)alkyl-$R_7$—($C_2$-$C_6$)alkenyl-, —($C_2$-$C_6$)alkenyl-$R_7$—($C_2$-$C_6$)alkenyl-, —($C_1$-$C_6$)alkyl-$R_7$—($C_2$-$C_6$)alkynyl-, —($C_2$-$C_6$)alkenyl-$R_7$—($C_2$-$C_6$)alkynyl-, —($C_2$-$C_6$)alkynyl-$R_7$—($C_2$-$C_6$)alkynyl-, —($C_2$-$C_6$)alkynyl-$R_7$—($C_1$-$C_6$)alkyl-, —($C_2$-$C_5$)alkynyl-$R_7$—($C_2$-$C_6$)alkenyl-, —($C_1$-$C_6$)alkyl-OCO—, or —$CH_2$—($CHOR_7$)$CH_2O$—($C_1$-$C_6$)alkyl-, where $R_7$ represents aryl, heteroaryl, ($C_3$-$C_8$)heterocyclyl, or ($C_3$-$C_{14}$)cycloalkyl, CORM represents a carbonyl metal complex chosen from among:

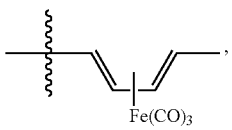

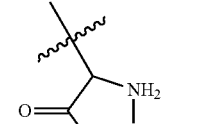

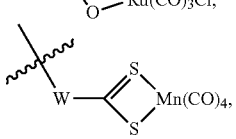

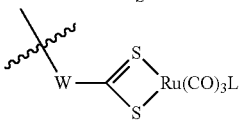

 and 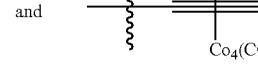

where W represents O or $NR_8$, where $R_8$ represents —($C_1$-$C_6$)alkyl-,

L represents an ionic ligand such as halogen, or a counterion such as $BF_4$ or $PF_6$, M represents Rh, Co, Ru, Mn, Mo, V or Fe, preferably Co, Ru or Mn, and n is an integer chosen so that the metal M has no free valency, and $R_1$ to $R_5$ represent independently:

H, —OH, —O($C_1$-$C_6$)alkyl, $SO_3H$, S($C_1$-$C_6$)alkyl, $NR_xR_y$, or $NR_xR_yR_z^+$ where $R_x$, $R_y$ and $R_z$ represent independently H or ($C_1$-$C_6$)alkyl;

or two consecutive radicals selected from $R_1$ to $R_5$, taken together, form a bridging group selected from the group consisting of —($CH_2$)$_m$—, or —O—($CH_2$)$_o$—O—, m being an integer between 3 and 5 and o being 1 or 2.

A second object of the invention is a compound of the following general formula (II):

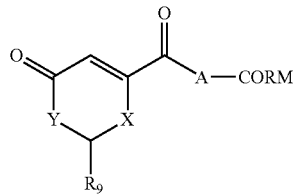

(II)

wherein:
A represents:
    a single bond, or
    -Q-Z—, where:
        Q represents O, S or $NR_6$, where $R_6$ represents H, ($C_1$-$C_6$)alkyl, aryl, heteroaryl, ($C_1$-$C_6$)alkyl-aryl, ($C_1$-$C_6$)alkyl-heteroaryl, ($C_1$-$C_6$)alkyl-($C_3$-$C_8$)heterocyclyl, —($C_3$-$C_{14}$)cycloalkyl, or $R_6$ and Z are connected to form a ($C_3$-$C_8$)heterocyclyl,
        Z represents —($C_1$-$C_6$)alkyl-, —($C_2$-$C_6$)alkenyl-, -aryl-, -heteroaryl-, —($C_2$-$C_6$)alkynyl-, —($C_3$-$C_8$)heterocyclyl-, —($C_3$-$C_{14}$)cycloalkyl, —($C_1$-$C_6$)alkyl-$R_7$—($C_1$-$C_6$)alkyl-, —($C_2$-$C_6$)alkenyl-$R_7$—($C_1$-$C_6$)alkyl-, —($C_1$-$C_6$)alkyl-$R_7$—($C_2$-$C_6$)alkenyl-, —($C_2$-$C_6$)alkenyl-$R_7$—($C_2$-$C_6$)alkenyl-, —($C_1$-$C_6$)alkyl-$R_7$—($C_2$-$C_6$)alkynyl-, —($C_2$-$C_6$)alkenyl-$R_7$—($C_2$-$C_6$)alkynyl-, —($C_2$-$C_6$)alkynyl-$R_7$—($C_2$-$C_6$)alkynyl-, —($C_2$-$C_6$)alkynyl-$R_7$—($C_1$-$C_6$)alkyl-, —($C_2$-$C_6$)alkynyl-$R_7$—($C_2$-$C_6$)alkenyl-, —($C_1$-$C_6$)alkyl-OCO—, or —$CH_2$—($CHOR_7$)$CH_2O$—($C_1$-$C_6$)alkyl-, where $R_7$ represents aryl, heteroaryl, ($C_3$-$C_8$)heterocyclyl, or ($C_3$-$C_{14}$)cycloalkyl, CORM represents a carbonyl metal complex chosen from among:

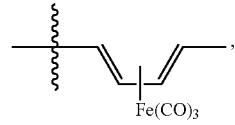

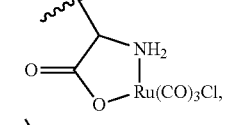

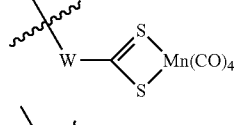

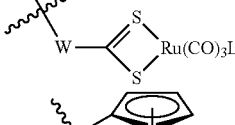

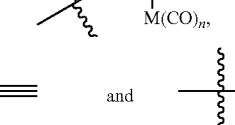

 and 

where W represents O or $NR_8$, where $R_8$ represents —$(C_1-C_6)$alkyl-,

L represents an ionic ligand such as halogen, or a counter-ion such as $BF_4$ or $PF_6$, M represents Rh, Co, Ru, Mn, Mo, V or Fe, preferably Co, Ru or Mn, and n is an integer chosen so that the metal M has no free valency, X represent $CR_{10}R_{11}$, O, S, or $NR_{12}$ Y represent $CR_{10}R_{11}$ if X represent O, S, or $NR_{12}$ otherwise Y represent O, S, or $NR_{12}$ where $R_{12}$ represent H, $(C_1-C_6)$alkyl, aryl, heteroaryl, $(C_1-C_6)$alkyl-aryl, $(C_1-C_6)$alkyl-heteroaryl or $(C_1-C_6)$alkyl-$(C_3-C_8)$heterocyclyl, —$(C_3-C_{14})$cycloalkyl, $R_9$ and the atom representing $CR_{10}R_{11}$ selected from X and Y, form together with the carbon atom bound to $R_9$, a ring selected from an aryl, an heteroaryl, an $(C_3-C_8)$heterocyclyl, or an $(C_3-C_{14})$cycloalkyl.

where $R_{10}$ and $R_{11}$ are selected in order to fulfill the requirement for said ring and, if not involved in said ring, can independently represent single bond, H, $(C_1-C_6)$alkyl, $(C_1-C_6)$alkenyl.

DETAILED DESCRIPTION OF THE INVENTION

Definitions

The present invention encompasses only stable compounds. In this regard, when "isomers" are referred to, only stable isomers are considered.

Within the groups, radicals or fragments defined in the description and the claims, the number of carbon atoms is specified inside the brackets. For example, $(C_1-C_6)$alkyl designates an alkyl group or radical having 1 to 6 carbon atoms.

In the formulas, $\xi$ indicates the bond linked to the rest of the molecule.

For the groups comprising two or more subgroups, the attachment is indicated with "-". For example, "—$(C_1-C_6)$alkyl-aryl-$(C_1-C_6)$alkenyl-" indicates a radical alkyl bound to a radical aryl itself bound to an alkenyl wherein the alkyl and alkenyl groups are bound to the rest of the molecule.

In the sense of the present invention, the expression "—$(C_1-C_6)$alkyl" designates an acyclic, saturated, linear or branched hydrocarbon chain comprising 1 to 6 carbon atoms. Examples of —$(C_1-C_6)$alkyl groups include methyl, ethyl, propyl, butyl, pentyl or hexyl. Unless explicitly stated, the definitions propyl, butyl, pentyl and hexyl include all possible isomers, in particular structural isomers. For example, butyl comprises n-butyl, iso-butyl, sec-butyl and tert-butyl. The alkyl group may be substituted, preferably with one or more groups independently selected from the group consisting of $(C_1-C_6)$alkyl, alkoxy, halogen, hydroxyl, amino, nitro, cyano, trifluoro, CHO, amide, cetone thiol, thioester, thioalkyl, urea, sulfoxyde sulfone, carboxylic acid or carboxylic ester In the sense of the present invention, the expression "—$(C_2-C_6)$alkenyl" designates an acyclic, saturated, linear or branched hydrocarbon chain comprising 2 to 6 carbon atoms, at least two of which are linked via a double bond. Examples of "—$(C_2-C_6)$alkenyl" include ethenyl or vinyl, propenyl, butenyl, pentenyl or hexenyl. Unless explicitly stated, the definitions of propenyl, butenyl, pentenyl and hexenyl include all possible isomers, in particular structural and/or position isomers.

In the sense of the present invention, the expression "—$(C_2-C_6)$alkynyl" designates an acyclic, saturated, linear or branched hydrocarbon chain comprising 2 to 6 carbon atoms, at least two of which are linked via a triple bond. Examples of "—$(C_2-C_6)$alkynyl" include ethynyl, propynyl, butynyl, pentynyl or hexynyl. Unless explicitly stated, the definitions of propynyl, butynyl, pentynyl and hexynyl include all possible isomers, in particular structural and/or position isomers.

The term substituted as used herein means that any of the hydrogen atoms can be replaced by a substituent, such as fluorine.

In the sense of the present invention, the expression "—$(C_3-C_{14})$cycloalkyl" designates a saturated or partially saturated mono-, di- or tri-cyclic structure comprising from 3 to 14 carbon atoms. Examples of "—$(C_3-C_{14})$cycloalkyl" include cyclopropyl, cyclobutyl, cyclopentyl, cyclohexyl, cycloheptyl, cyclooctyl, cyclopentenyl and cyclohexenyl.

Examples of "—$(C_3-C_8)$cycloalkyl" include cyclopropyl, cyclobutyl, cyclopentyl, cyclohexyl, cycloheptyl or cyclooctyl. Unless explicitly stated, the cycloalkyls can be substituted by one or more groups such as methyl, ethyl, isopropyl, hydroxy, fluoro, chloro, bromo and iodo.

In the sense of the present invention, the expression "—$(C_3-C_8)$heterocyclyl" designates saturated heterocycles having 3, 4, 5, 6, 7 or 8 atoms in the ring where 1, 2 or 3 heteroatoms chosen from among N, O and S replace the corresponding number of carbon atoms. Examples of "—$(C_3-C_8)$heterocyclyl" include aziridinyl, oxyranyl, pyrrolidinyl, tetrahydrofuranyl, oxazolyl, piperidinyl, piperazinyl and morpholinyl.

The term "aryl" designates an aromatic, monocyclic ring that may be fused with a second saturated, unsaturated or aromatic ring. The term aryl include, without restriction to the following examples, phenyl, indanyl, indenyl, naphtyl, anthracenyl, phenanthrenyl, tetrahydronaphtyl and dihydronaphtyl. The most preferred aryl are those comprising one six-membered aromatic ring. The aryl group may be substituted, preferably with one or more groups independently selected from the group consisting of $(C_1-C_6)$alkyl, alkoxy, halogen, hydroxyl, amino, nitro, cyano, trifluoro, CHO, amide, cetone thiol, thioester, thioalkyl, urea, sulfoxyde sulfone, carboxylic acid or carboxylic ester.

The term heteroaryl designates a mono- or polycyclic aryl as defined above where one or more carbon atoms have been replaced with one or more heteroatoms chosen from among N, O and S. Unless explicitly stated, the term "heteroaryl" includes all possible isomers, in particular position isomers.

Examples of heteroaryl groups include furyl, thienyl, imidazolyl, pyridyl, pyrrolyl, N-alkyl pyrrolyl, pyrimidinyl, pyrazinyl, tetrazolyl, triazolyl and triazinyl. The heteroaryl group may be substituted, preferably with one or more groups independently selected from the group consisting of alkyl, alkoxy, halogen, hydroxyl, amino, nitro, cyano, trifluoro, carboxylic acid or carboxylic ester. Preferred heteroaryls are those having 5 or 6 atoms in the ring, such as indolyl, pyrrolyl, pyridinyl, pyrrazolyl, triazolyl, furanyl or thienyl.

As used, herein, the term "halogen" designates a fluorine, chlorine, bromine or iodine atom.

For the purpose of the invention, the term "pharmaceutically acceptable" is intended to mean what is useful to the preparation of a pharmaceutical composition, and what is generally safe and non-toxic, for a pharmaceutical use.

The term «pharmaceutically acceptable salt, hydrate of solvate» is intended to mean, in the framework of the present invention, a salt of a compound which is pharmaceutically acceptable, as defined above, and which possesses the pharmacological activity of the corresponding compound. Such salts comprise:

(1) hydrates and solvates, (2) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and (3) salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

Caffeic Acids Derivatives CORM

In a first aspect, the invention concerns a hybrid caffeic acid-carbon monoxide releasing molecule (caffeic acid-CO-RM), in which the caffeic acid moiety is substituted by a CO-releasing carbonyl complex, of formula (I):

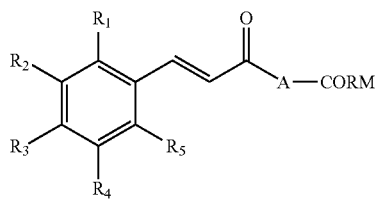

(I)

wherein:

A represents:

a single bond, or

-Q-Z—, where:

Q represents O, S or $NR_6$, where $R_6$ represents H, $(C_1-C_6)$alkyl, aryl, heteroaryl, $(C_1-C_6)$alkyl-aryl, $(C_1-C_6)$alkyl-heteroaryl or $(C_1-C_6)$alkyl-$(C_3-C_8)$heterocyclyl, —$(C_3-C_{14})$cycloalkyl, or $R_6$ and Z are connected to form a $(C_3-C_8)$heterocyclyl, Z represents —$(C_1-C_6)$alkyl-, —$(C_2-C_6)$alkenyl-, -aryl-, -heteroaryl-, —$(C_2-C_6)$alkynyl-, —$(C_3-C_8)$heterocyclyl-, —$(C_3-C_{14})$cycloalkyl, —$(C_1-C_6)$alkyl-$R_7$—$(C_1-C_6)$alkyl-, —$(C_2-C_6)$alkenyl-$R_7$—$(C_1-C_6)$alkyl-, —$(C_1-C_6)$alkyl-$R_7$—$(C_2-C_6)$alkenyl-, —$(C_2-C_6)$alkenyl-$R_7$—$(C_2-C_6)$alkenyl-, —$(C_1-C_6)$alkyl-$R_7$—$(C_2-C_6)$alkynyl-, —$(C_2-C_6)$alkenyl-$R_7$—$(C_2-C_6)$alkynyl-, —$(C_2-C_6)$alkynyl-$R_7$—$(C_2-C_6)$alkynyl-, —$(C_2-C_6)$alkynyl-$R_7$—$(C_1-C_6)$alkyl-, —$(C_2-C_6)$alkynyl-$R_7$—$(C_2-C_6)$alkenyl-, —$(C_1-C_6)$alkyl-OCO—, or —$CH_2$—$(CHOR_7)$ $CH_2O$—$(C_1-C_6)$alkyl-, where $R_7$ represents aryl, heteroaryl, $(C_3-C_8)$heterocyclyl, or $(C_3-C_{14})$cycloalkyl, CORM represents a carbonyl metal complex chosen from among:

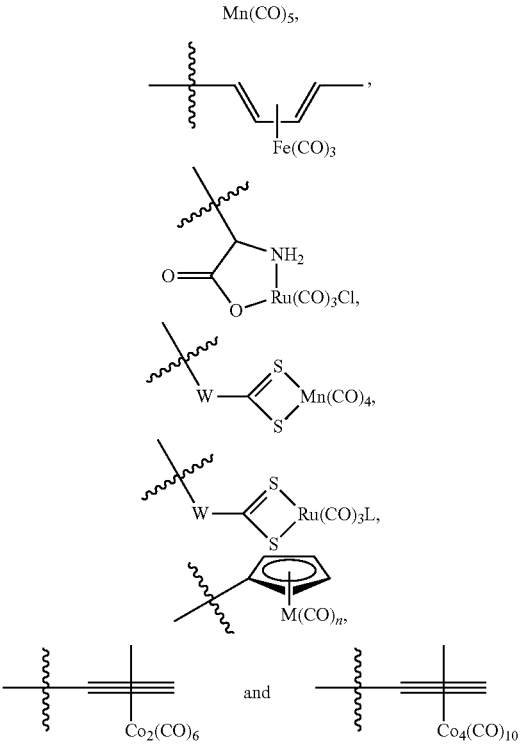

where W represents O or $NR_8$, where $R_8$ represents —$(C_1-C_6)$alkyl-,

L represents an ionic ligand such as halogen, or a counter-ion such as $BF_4$ or $PF_6$, M represents Rh, Co, Ru, Mn, Mo, V or Fe, preferably Co, Ru or Mn, and n is an integer chosen so that the metal M has no free valency, and $R_1$ to $R_5$ represent independently:

H, —OH, —O$(C_1-C_6)$alkyl, $SO_3H$, $S(C_1-C_6)$alkyl, $NR_xR_y$, or $NR_xR_yR_z+$ where $R_x$, $R_y$ and $R_z$ represent independently H or $(C_1-C_6)$alkyl;

or two consecutive radical selected from $R_1$ to $R_5$, taken together, form a bridging group selected from the group consisting of —$(CH_2)_m$—, or —O—$(CH_2)_o$—O—, m being an integer between 3 and 5 and o being 1 or 2.

Those compounds, when incubated with cells, release an amount of CO comparable with conventional CORM such as CORM-401 and, as it has been shown in vivo, they induce a release of CO which can be confirmed by the presence of carbonmonoxy hemoglobin (HbCO) in blood 6 hours after oral administration.

For example, compounds B and C of the examples below, illustrative of the compounds of formula (I) described thereafter, are capable of releasing a significant amount of CO under the in vitro conditions described in the examples. Those compounds were also shown to enhance nuclear expression of Nrf2 (two fold increase), HO-1 protein expression (two fold increase), and a higher anti-inflammatory potential than known compounds. Hence, these compounds are promising compounds to up-regulate tissue HO-1 and deliver CO in vivo.

Moreover, it has been found by the inventors that the substituents on the phenyl group are of utmost importance for both stability and activity of those hybrids.

Indeed, —OH groups on the phenyl can have a detrimental effect on the stability of the hybrid CORM. Furthermore, they found that methoxy groups will allow the molecule to stay stable in time and will enhance the Nrf2/HO-1 activation properties of the hybrids.

Hence, preferably, $R_1$ to $R_5$ represent independently H or —O($C_1$-$C_6$)alkyl.

More preferably, $R_1$ to $R_5$ represent independently H or —O($C_1$-$C_6$)alkyl and at least two groups from $R_1$ to $R_5$ represent —O($C_1$-$C_6$)alkyl, preferably —$OCH_3$.

Particularly, among $R_1$ to $R_5$, two consecutive radical selected from $R_1$ to $R_5$, taken together, form a bridging group selected from the group consisting of —$(CH_2)_m$—, or —O—$(CH_2)_o$—O—, m being an integer between 3 and 5 and o being 1 or 2.

Preferably, among $R_1$ to $R_5$, two consecutive radical selected from $R_1$ to $R_5$, taken together, form a bridging group selected from the group consisting of —O—$(CH_2)_o$—O— with o being 1 or 2.

Even more preferably $R_1$ to $R_5$ are chosen as in table 1:

TABLE 1

| R1 | R2 | R3 | R4 | R5 |
|----|----|----|----|----|
| OMe | H | H | H | H |
| OMe | H | H | H | OMe |
| OMe | H | OMe | H | H |
| OMe | H | H | OMe | H |
| OMe | OMe | H | H | H |
| OMe | H | OMe | H | OMe |
| OMe | OMe | OMe | H | H |
| OMe | OMe | H | OMe | H |
| OMe | H | OMe | OMe | H |
| H | OMe | OMe | H | H |
| H | OMe | OMe | OMe | H |

Beside, hybrids molecules were evaluated for their two opposing actions: cytotoxicity and cytoprotective effects. As shown in examples, compounds according to formula I have a lower impact on GSH compared to dimethylfumarate (DMF) but have a more potent induction of Nrf2 and HO-1 pathways. Hence they induce the expression of the antioxidant and protective protein HO-1 and do not cause a decrease in GSH but actually increase it over time.

Advantageously, the compound of formula (I) is chosen from among:

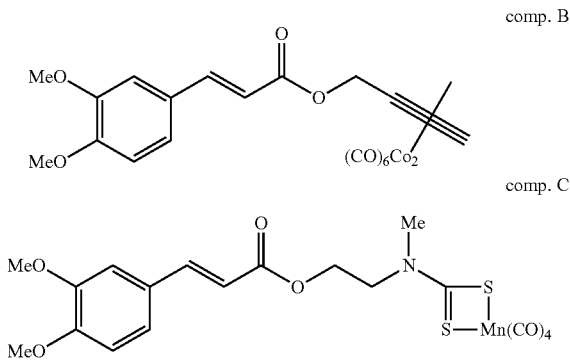

Heterocyclic Derivatives CORM

According to a second aspect, the invention concerns a new hybrid structure comprising a heterocycle moiety and a carbon monoxide releasing molecule (COM), in which the moiety comprising the heterocycle bear a conjugated ene-dicarbonyl system and is substituted by a CO-releasing carbonyl complex, of formula (II):

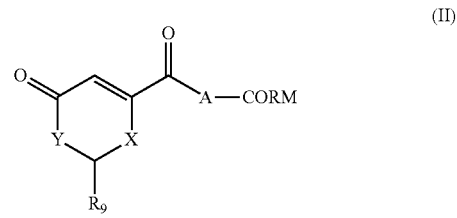

wherein:
A represents:
  a single bond, or
  -Q-Z—, where:
    Q represents O, S or $NR_6$, where $R_6$ represents H, ($C_1$-$C_6$)alkyl, aryl, heteroaryl, ($C_1$-$C_6$)alkyl-aryl, ($C_1$-$C_6$)alkyl-heteroaryl or ($C_1$-$C_6$)alkyl-($C_3$-$C_8$)heterocyclyl, —($C_3$-$C_{14}$)cycloalkyl, or $R_6$ and Z are connected to form a ($C_3$-$C_8$)heterocyclyl,
    Z represents —($C_1$-$C_6$)alkyl-, —($C_2$-$C_6$)alkenyl-, -aryl-, -heteroaryl-, —($C_2$-$C_6$)alkynyl-, —($C_3$-$C_8$) heterocyclyl-, —($C_3$-$C_{14}$)cycloalkyl, —($C_1$-$C_6$) alkyl-$R_7$—($C_1$-$C_6$)alkyl-, —($C_2$-$C_6$)alkenyl-$R_7$— ($C_1$-$C_6$)alkyl-, —($C_1$-$C_6$)alkyl-$R_7$—($C_2$-$C_6$) alkenyl-, —($C_2$-$C_6$)alkenyl-$R_7$—($C_2$-$C_6$)alkenyl-, —($C_1$-$C_6$)alkyl-$R_7$—($C_2$-$C_6$)alkynyl-, —($C_2$-$C_6$) alkenyl-R—($C_2$-$C_6$)alkynyl-, —($C_2$-$C_6$)alkynyl-$R_7$—($C_2$-$C_6$)alkynyl-, —($C_2$-$C_6$)alkynyl-$R_7$—($C_1$-$C_6$)alkyl-, —($C_2$-$C_6$)alkynyl-$R_7$—($C_2$-$C_6$)alkenyl-, —($C_1$-$C_6$)alkyl-OCO—, or —$CH_2$—(CHO$R_7$) $CH_2$O—($C_1$-$C_6$)alkyl-, where $R_7$ represents aryl, heteroaryl, ($C_3$-$C_8$)heterocyclyl, or ($C_3$-$C_{14}$)cycloalkyl, CORM represents a carbonyl metal complex chosen from among:

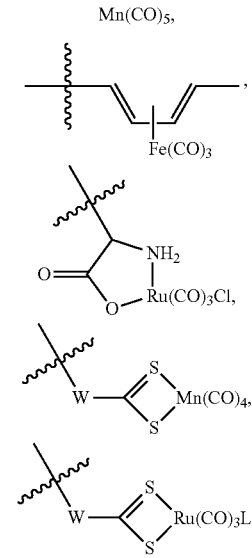

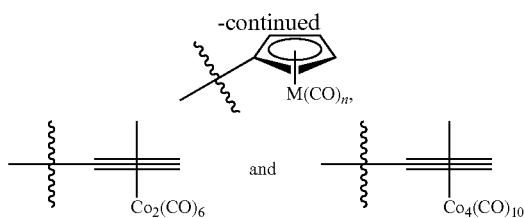

where W represents O or $NR_8$, where $R_8$ represents —$(C_1-C_6)$alkyl-

L represents an ionic ligand such as halogen, or a counter-ion such as $BF_4$ or $PF_6$, M represents Rh, Co, Ru, Mn, Mo, V or Fe, preferably Co, Ru or Mn, and n is an integer chosen so that the metal M has no free valency, X represent $CR_{10}R_{11}$, O, S, or $NR_{12}$, Y represent $CR_{10}R_{11}$ if X represent O, S, or $NR_{12}$ otherwise Y represent O, S, or $NR_{12}$ where $R_{12}$ represent H, $(C_1-C_6)$alkyl, aryl, heteroaryl, $(C_1-C_6)$alkyl-aryl, $(C_1-C_6)$alkyl-heteroaryl or $(C_1-C_6)$alkyl-$(C_3-C_8)$heterocyclyl, —$(C_3-C_{14})$cycloalkyl, $R_9$ and the atom representing $CR_{10}R_{11}$ selected from X and Y, form together with the carbon atom bound to $R_9$, a ring selected from an aryl, an heteroaryl, an $(C_3-C_8)$heterocyclyl, or an $(C_3-C_{14})$cycloalkyl.

where $R_{10}$ and $R_{11}$ are selected in order to fulfill the requirement for said ring and, if not involved in said ring, can independently represent single bond, H, $(C_1-C_6)$alkyl, $(C_1-C_6)$alkenyl.

Unexpectedly, it has been found that compounds of formula (II) are capable of releasing CO at a fast rate.

For example, compound A of the examples below, illustrative of the compounds of formula (II), is capable of releasing CO with a half-life of less than 25 minutes under the in vitro conditions described in the examples, which is an ultra-fast rate in the sense of the present invention.

Indeed, compounds of formula (II) are therefore advantageous for a relatively fast biological activity. Compared to the previously developed fumarate derivatives —CORM (HYCO-1), the semi-cyclized fumarate-CORM of the present invention release CO almost twice faster and, at 60 min, it has released more than 2 fold the amount of CO released by HYCO-1.

Moreover, experiments demonstrate that compounds of the invention are potent activators of Nrf2 and inducers of HO-1 protein expression.

Hence, comparison between compounds according to this formula and previously disclosed compounds such as HYCO-1 from (Wilson et al. Chem. Eur. J. 2014, 20, 14698-14704) show that the semi cyclisation of the fumarate induce a much faster and larger release of CO compared to linear fumarate derivative-CORM.

Such a fast release of CO permits a first prevention of damage through CO delivery until the subsequent promotion of the endogenous up-regulation of Nrf2-dependent defensive proteins and thus induce overall a greater and long-lasting tissue protection.

Beside, hybrids molecules were evaluated for their two opposing actions: cytotoxicity and cytoprotective effects. As shown in examples, compounds according to formula I have a lower impact on GSH compared to dimethylfumarate (DMF) but have a more potent induction of Nrf2 and HO-1 pathways. Hence they induce the expression of the antioxidant and protective protein HO-1 and do not cause a decrease in GSH but actually increase it over time.

In particular X represent $CR_{10}R_{11}$, S or O

Preferably X represent $CR_{10}R_{11}$ or O

In particular, Y represent $CR_{10}R_{11}$ if X represent O, S, or $NR_{12}$ otherwise Y represent O, or S Preferably, Y represent $CR_{10}R_{11}$ if X represent O, S, or $NR_{12}$ otherwise Y represent O In particular $R_{12}$ represents H, $(C_1-C_6)$alkyl, aryl, heteroaryl, $(C_1-C_6)$alkyl-aryl, $(C_1-C_6)$alkyl-heteroaryl or $(C_1-C_6)$alkyl-$(C_3-C_8)$heterocyclyl, or —$(C_3-C_{14})$cycloalkyl, Preferably $R_{12}$ represents H, aryl, heteroaryl, or $(C_1-C_6)$alkyl More preferably $R_{12}$ represents H, or $(C_1-C_6)$alkyl $R_9$ and the atom representing $CR_{10}R_{11}$ selected from X and Y, form together with the carbon atom bound to $R_9$, a ring selected from an aryl, an heteroaryl, an $(C_3-C_8)$heterocyclyl, or an $(C_3-C_{14})$cycloalkyl.

where $R_{10}$ and $R_{11}$ are selected in order to fulfill the requirement for said ring and, if not involved in said ring, can independently represent single bond, H, $(C_1-C_6)$alkyl, $(C_1-C_6)$alkenyl.

Preferably, $R_9$ and the atom representing $CR_{10}R_{11}$ selected from X and Y, form together with the carbon atom bound to $R_9$, a ring selected from an aryl, or an heteroaryl, more preferably an aryl According to a first embodiment, the invention concerns a hybrid Chromone-carbon monoxide releasing molecule (Chromone-CO-RM), in which the Chromone moiety is substituted by a CO-releasing carbonyl complex, of formula (IIa):

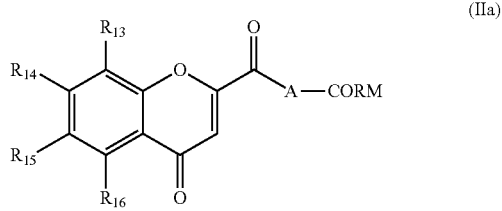

wherein:

A represents:
a single bond, or
-Q-Z—, where:
Q represents O, S or $NR_6$, where $R_6$ represents H, $(C_1-C_6)$alkyl, aryl, heteroaryl, $(C_1-C_6)$alkyl-aryl, $(C_1-C_6)$alkyl-heteroaryl or $(C_1-C_6)$alkyl-$(C_3-C_8)$heterocyclyl, —$(C_3-C_{14})$cycloalkyl, or $R_6$ and Z are connected to form a $(C_3-C_8)$heterocyclyl, Z represents —$(C_1-C_6)$alkyl-, —$(C_2-C_6)$alkenyl-, -aryl-, -heteroaryl-, —$(C_2-C_6)$alkynyl-, —$(C_3-C_8)$heterocyclyl-, —$(C_3-C_{14})$cycloalkyl, —$(C_1-C_6)$alkyl-$R_7$—$(C_1-C_6)$alkyl-, —$(C_2-C_6)$alkenyl-$R_7$—$(C_1-C_6)$alkyl-, —$(C_1-C_6)$alkyl-$R_7$—$(C_2-C_6)$alkenyl-, —$(C_2-C_6)$alkenyl-$R_7$—$(C_2-C_6)$alkenyl-, —$(C_1-C_6)$alkyl-$R_7$—$(C_2-C_6)$alkynyl-, —$(C_2-C_6)$alkenyl-$R_7$—$(C_2—C)$alkynyl-, —$(C_2-C_6)$alkynyl-$R_7$—$(C_2-C_6)$alkynyl-, —$(C_2-C_6)$alkynyl-$R_7$—$(C_1-C_6)$alkyl-, —$(C_2-C_6)$alkynyl-$R_7$—$(C_2-C_6)$alkenyl-, —$(C_1-C_6)$alkyl-OCO—, or —$CH_2$—$(CHOR_7)$ $CH_2O$—$(C_1-C_6)$alkyl-, where $R_7$ represents aryl, heteroaryl, $(C_3-C_8)$heterocyclyl, or $(C_3-C_{14})$cycloalkyl, CORM represents a carbonyl metal complex chosen from among:

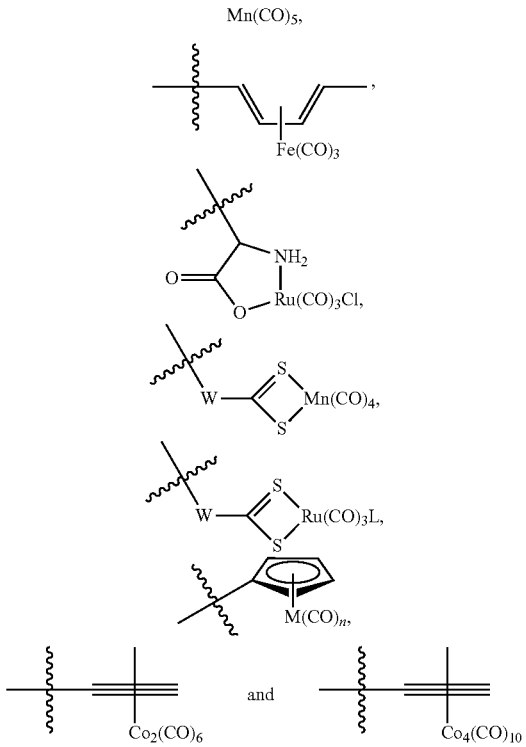

where W represents O or $NR_8$, where $R_8$ represents —($C_1$-$C_6$)alkyl-

L represents an ionic ligand such as halogen, or a counter-ion such as $BF_4$ or $PF_6$, M represents Rh, Co, Ru, Mn, Mo, V or Fe, preferably Co, Ru or Mn, and n is an integer chosen so that the metal M has no free valency, and $R_{13}$ to $R_{16}$ represent independently:

H, halogen, —CN, —$NO_2$, —NO, —CHO, —$NR_xR_y$, —$NR_xR_yR_z+$, —$SO_3H$, —$CO_2R_x$, —$SO_2R_x$, —$SO_2NR_xR_y$, —OH, —$OR_x$, —$COR_y$, —$SR_x$, —$CONR_xR_y$, —$SO_2(O)R_x$, a group selected from saturated ($C_1$-$C_6$)alkyl or unsaturated ($C_1$-$C_6$)alkyl, where $R_x$ $R_y$ and $R_z$ represent independently H or ($C_1$-$C_6$)alkyl, or two consecutive radical selected from $R_{13}$ to $R_{16}$, taken together, form a bridging group selected from the group consisting of —$(CH_2)_m$—, or —O—$(CH_2)_o$—O—, m being an integer between 3 and 5 and o being 1 or 2.

Preferably $R_{13}$ to $R_{16}$ represent independently: H, —OH, —O($C_1$-$C_6$)alkyl or saturated ($C_1$-$C_6$)alkyl, More preferably $R_{13}$ to $R_{16}$ represent independently: H or —$OCH_3$.

Particularly, among $R_{13}$ to $R_{16}$, two consecutive radical selected from $R_{13}$ to $R_{16}$, taken together, form a bridging group selected from the group consisting of —$(CH_2)_m$—, or —O—$(CH_2)_o$—O—, m being an integer between 3 and 5 and o being 1 or 2.

Preferably, among $R_{13}$ to $R_{16}$, two consecutive radical selected from $R_{13}$ to $R_{16}$, taken together, form a bridging group selected from the group consisting of —O—$(CH_2)_o$—O— with o being 1 or 2.

Even more preferably $R_{13}$ to $R_{16}$ are chosen as in table 2:

TABLE 2

| R13 | R14 | R15 | R16 |
|---|---|---|---|
| OMe | H | H | H |
| H | OMe | H | H |
| H | H | OMe | H |
| H | H | H | OMe |
| OMe | H | OMe | H |
| OMe | H | H | OMe |
| H | OMe | OMe | H |

Advantageously, the compound of formula (IIa) is chosen from among:

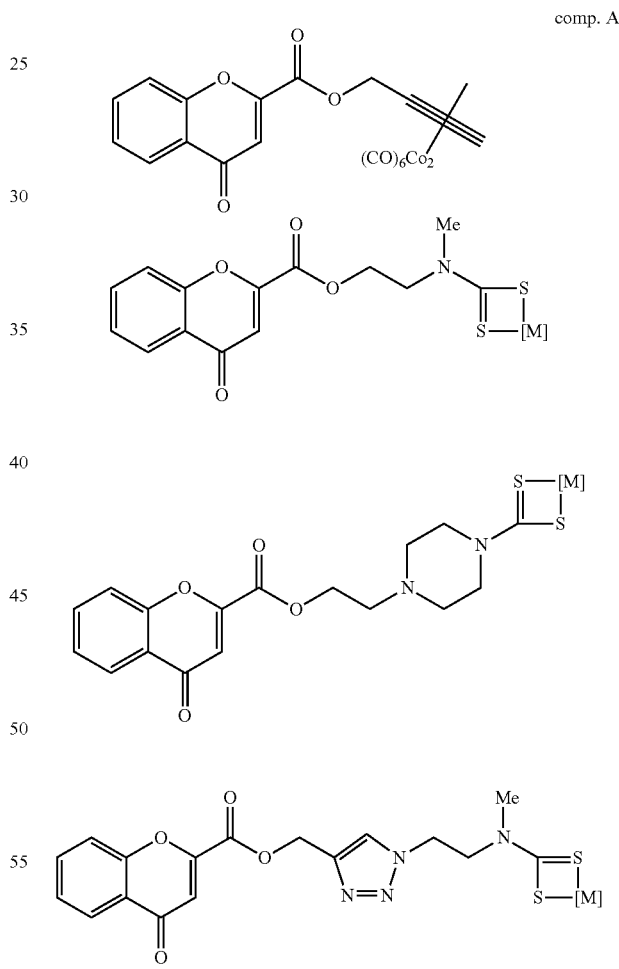

comp. A where [M]=$Mn(CO)_4$ or $Ru(CO)_3Cl$

According to a second embodiment, the invention concerns a hybrid coumarin-carbon monoxide releasing molecule (Coumarin-CO-RM), in which the Coumarin moiety is substituted by a CO-releasing carbonyl complex, of formula (IIb):

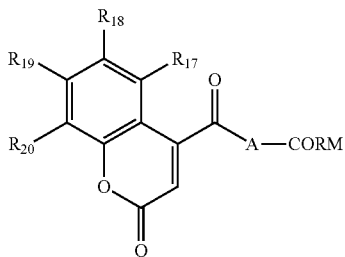

(IIb)

wherein:

A represents:
  single bond, or
  -Q-Z—, where:
    Q represents O, S or $NR_6$, where $R_6$ represents H, $(C_1-C_6)$alkyl, aryl, heteroaryl, $(C_1-C_6)$alkyl-aryl, $(C_1-C_6)$alkyl-heteroaryl or $(C_1-C_6)$alkyl-$(C_3-C)$ heterocyclyl, —$(C_3-C_{14})$cycloalkyl, or $R_6$ and Z are connected to form a $(C_3-C_8)$heterocyclyl,
    Z represents —$(C_1-C_6)$alkyl-, —$(C_2-C_6)$alkenyl-, -aryl-, -heteroaryl-, —$(C_2-C_6)$alkynyl-, —$(C_3-C_8)$ heterocyclyl-, —$(C_3-C_{14})$cycloalkyl-, —$(C_1-C_6)$ alkyl-$R_7$—$(C_1-C_6)$alkyl-, —$(C_2-C_6)$alkenyl-$R_7$— $(C_1-C_6)$alkyl-, —$(C_1-C_6)$alkyl-$R_7$—$(C_2-C_6)$ alkenyl-, —$(C_2-C_6)$alkenyl-$R_7$—$(C_2-C_6)$alkenyl-, —$(C_1-C_6)$alkyl-$R_7$—$(C_2-C_6)$alkynyl-, —$(C_2-C_6)$ alkenyl-$R_7$—$(C_2-C_6)$alkynyl-, —$(C_2-C_6)$alkynyl-$R_7$—$(C_2-C_6)$alkynyl-, —$(C_2-C_6)$alkynyl-$R_7$—$(C_1-C_6)$alkyl-, —$(C_2-C_6)$alkynyl-$R_7$—$(C_2-C_6)$alkenyl-, —$(C_1-C_6)$alkyl-OCO—, or —$CH_2$—$(CHOR_7)$ $CH_2O$—$(C_1-C_6)$alkyl-, where $R_7$ represents aryl, heteroaryl, $(C_3-C_8)$heterocyclyl, or $(C_3-C_{14})$cycloalkyl,
CORM represents a carbonyl metal complex chosen from among:

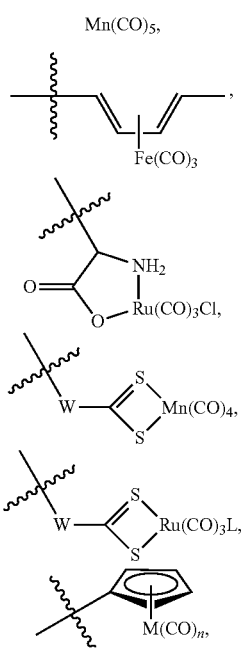

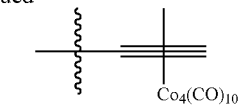

where W represents O or $NR_8$, where $R_8$ represents —$(C_1-C_6)$alkyl-

L represents an ionic ligand such as halogen, or a counterion such as $BF_4$ or $PF_6$, M represents Rh, Co, Ru, Mn, Mo, V or Fe, preferably Co, Ru or Mn, and n is an integer chosen so that the metal M has no free valency, and $R_{17}$ to $R_{20}$ represent independently:

H, halogen, —CN, —$NO_2$, —NO, —CHO, —$NR_xR_y$, —$NR_xR_yR_z+$, —$SO_3H$, —$CO_2R_x$, —$SO_2R_x$, —$SO_2NR_xR_y$, —OH, —$OR_x$, —$COR_y$, —$SR_x$, —$CONR_xR_y$, —$SO_2(O)R_x$, a group selected from saturated $(C_1-C_6)$alkyl or unsaturated $(C_1-C_6)$alkyl, where $R_x$ $R_y$ and R represent independently H or $(C_1-C_6)$alkyl, or two consecutive radicals selected from $R_{17}$ to $R_{20}$, taken together, form a bridging group selected from the group consisting of —$(CH_2)_m$—, or —O— $(CH_2)$—O—, m being an integer between 3 and 5 and o being 1 or 2.

Preferably $R_{17}$ to $R_{20}$ represent independently: H, —OH, —$O(C_1-C_6)$alkyl, or saturated $(C_1-C_6)$alkyl, More preferably $R_{17}$ to $R_{20}$ represent independently: H or —$OCH_3$.

Particularly, among $R_{17}$ to $R_{20}$, two consecutive radicals selected from $R_{17}$ to $R_{20}$, taken together, form a bridging group selected from the group consisting of —$(CH_2)_m$—, or —O—$(CH_2)_o$—O—, m being an integer between 3 and 5 and o being 1 or 2.

Preferably, among $R_{17}$ to $R_{20}$, two consecutive radicals selected from $R_{17}$ to $R_{20}$, taken together, form a bridging group selected from the group consisting of —O—$(CH_2)_o$—O— with o being 1 or 2.

Even more preferably $R_{17}$ to $R_{20}$ are chosen as in table 3:

TABLE 3

| R17 | R18 | R19 | R20 |
|-----|-----|-----|-----|
| OMe | H | H | H |
| H | OMe | H | H |
| H | H | OMe | H |
| H | OMe | OMe | H |

CORM Structures

For all objects and embodiments described of the invention, preferred definitions of A and CORM are as follow:

A represents:
  a single bond, or
  —Z-Q—, where:
    Q represents O, S or $NR_6$, where $R_6$ represents H, $(C_1-C_6)$alkyl, aryl, heteroaryl, $(C_1-C_6)$alkyl-aryl, $(C_1-C_6)$alkyl-heteroaryl or $(C_1-C_6)$alkyl-$(C_3-C_8)$heterocyclyl, —$(C_3-C_{14})$cycloalkyl, or $R_6$ and Z are connected to form a $(C_3-C_8)$heterocyclyl,
    Z represents —$(C_1-C_6)$alkyl-, —$(C_2-C_6)$alkenyl-, -aryl-, -heteroaryl-, —$(C_2-C_6)$alkynyl-, —$(C_3-C_8)$ heterocyclyl-, —$(C_3-C_{14})$cycloalkyl-, —$(C_1-C_6)$ alkyl-$R_7$—$(C_1-C_6)$alkyl-, —$(C_2-C_6)$alkenyl-$R_7$— $(C_1-C_6)$alkyl-, —$(C_1-C_6)$alkyl-$R_7$—$(C_2-C_6)$ alkenyl-, —$(C_2-C_6)$alkenyl-$R_7$—$(C_2-C_5)$alkenyl-, —$(C_1-C_6)$alkyl-$R_7$—$(C_2-C_6)$alkynyl-, —$(C_2-C_8)$ alkenyl-R$_7$—(C$_2$-C$_6$)alkynyl-, —(C$_2$-C$_6$)alkynyl-R$_7$—(C$_2$-C$_6$)alkynyl-, —(C$_2$-C$_6$)alkynyl-R$_7$—(C$_1$-C$_6$)alkyl-, —(C$_2$-C$_6$)alkynyl-R$_7$—(C$_2$-C$_6$)alkenyl-, —(C$_1$-C$_6$)alkyl-OCO—, or —CH$_2$—(CHOR$_7$)CH$_2$O—(C$_1$-C$_6$)alkyl-, where R$_7$ represents aryl, heteroaryl, (C$_3$-C$_8$)heterocyclyl, or (C$_3$-C$_{14}$)cycloalkyl, Advantageously, Q represents O, S or NR$_6$, where R$_6$ represents H, —(C$_1$-C$_6$)alkyl and Z represents —(C$_1$-C$_6$)alkyl-, —(C$_2$-C$_6$)alkenyl-, —(C$_3$-C$_8$)heterocyclyl-, —(C$_1$-C$_6$)alkyl-R$_7$—(C$_1$-C$_6$)alkyl-, or —(C$_2$-C$_6$)alkenyl-R$_7$—(C$_1$-C$_6$)alkyl-, where R$_7$ represents heteroaryl or (C$_3$-C$_8$)heterocyclyl More, advantageously, Q represents O or NR$_6$, preferably O and R$_6$ represents H or —(C$_1$-C$_6$)alkyl.

Advantageously, Z represents —(C$_1$-C$_6$)alkyl-, —(C$_2$-C$_6$)alkenyl-, —(C$_3$-C$_8$)heterocyclyl-, —(C$_1$-C$_6$)alkyl-R$_7$—(C$_1$-C$_6$)alkyl-, —(C$_2$-C$_6$)alkenyl-R$_7$—(C$_1$-C$_6$)alkyl- where R$_7$ represents heteroaryl or (C$_3$-C$_8$)heterocyclyl.

preferably, CORM represents a carbonyl metal complex chosen from among:

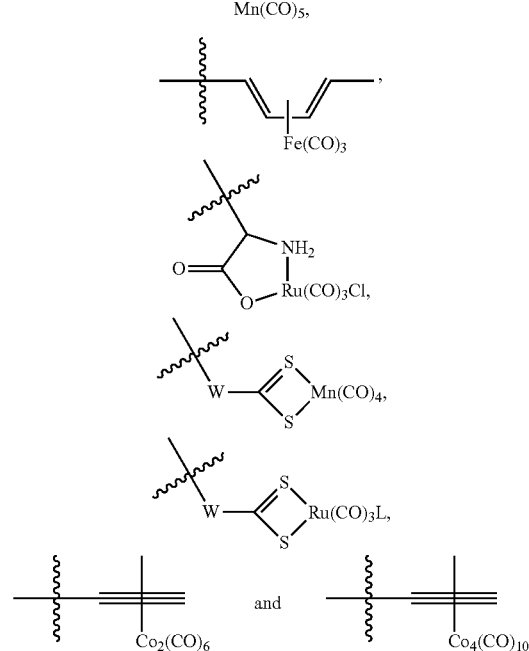

where W represents O or NR$_8$, where R$_8$ represents —(C$_1$-C$_6$)alkyl-,

L represents an ionic ligand such as halogen, or a counter-ion such as BF$_4$ or PF$_6$, Advantageously, CORM is chosen from among:

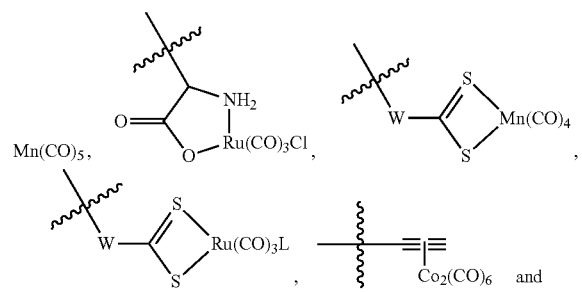

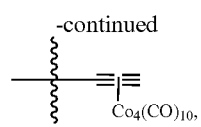

more advantageously from among:

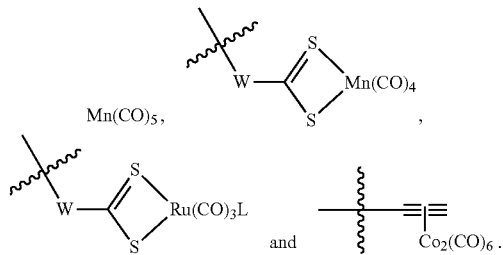

even more advantageously from among:

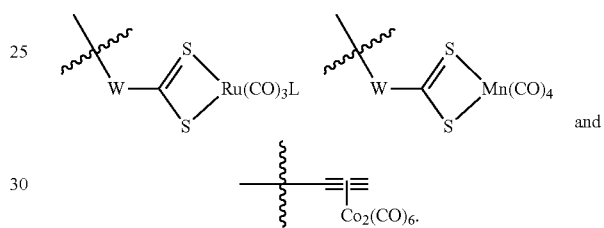

where W represents O or NR$_8$, where R$_8$ represents —(C$_1$-C$_6$)alkyl-

Indeed it has be shown that hybrids bearing such CORM are more efficient in CO release than other CORM.

Particularly, Q is O or NR$_6$, preferably O.

The invention also concerns a pharmaceutical composition comprising at least one compound of the invention, a pharmaceutically acceptable salt, solvate or hydrate thereof, as defined previously and at least one pharmaceutically acceptable excipient.

The pharmaceutical compositions of the invention are advantageously suitable for administration via oral, sublingual, subcutaneous, intramuscular, intravenous, transdermal, topical or rectal route. The pharmaceutical compositions of the invention may also be administered by inhalation, for example by means of an aerosol. The active ingredient can be administered in unit forms for administration, mixed with conventional pharmaceutical carriers, to animals or to humans.

When a solid composition is prepared in the form of tablets, the main active ingredient is mixed with a pharmaceutical vehicle and other conventional excipients known to those skilled in the art.

The compounds of the invention can be used in a pharmaceutical composition at a dose ranging from 0.01 mg to 1000 mg a day, administered in only one dose once a day or in several doses along the day, for example twice a day. The daily administered dose is advantageously comprised between 5 mg and 500 mg, and more advantageously between 10 mg and 200 mg. However, it can be necessary to use doses out of these ranges, which could be noticed by the person skilled in the art.

The present invention further concerns a compound of the invention, a pharmaceutically acceptable salt, solvate or hydrate thereof, or a pharmaceutical composition comprising at least one compound of the invention, a salt, solvate or hydrate thereof, for use as a drug.

The present invention further concerns at least one compound of the invention, a pharmaceutically acceptable salt, solvate or hydrate thereof, or a pharmaceutical composition comprising at least one compound of the invention, a salt, solvate or hydrate thereof, for use in the treatment of cardiovascular or inflammatory diseases.

The present invention further concerns the use of at least one compound of the invention, a pharmaceutically acceptable salt, solvate or hydrate thereof, for the manufacture of a medicament for use in the treatment of cardiovascular or inflammatory diseases.

The present invention further concerns a method for treating cardiovascular or inflammatory diseases, comprising the administration of at least one compound of the invention, a pharmaceutically acceptable salt, solvate or hydrate thereof, or of a pharmaceutical composition comprising at least one compound of the invention, a pharmaceutically acceptable salt, solvate or hydrate thereof, to a person in need thereof.

Inflammatory and cardiovascular diseases according to the present invention include for example myocardial ischemia and heart diseases, rheumatoid arthritis, acute and chronic skin wound (wound healing), inflammatory bowel disease, post-operative ileus, brain ischemia, psoriasis, diabetes, diabetic nephropathy, metabolic syndrome, sickle-cell disease, neurodegenerative diseases such as Alzheimer's disease or Parkinson's disease, neuropathic pain, hypertension, pulmonary arterial hypertension, septicemia, septic or endotoxic shock, hemorrhagic shock, multiple sclerosis, cancer and chronic obstructive pulmonary disease. Preferred inflammatory and cardiovascular diseases according to the present invention are skin wound (wound healing), brain and cardiac ischemia, psoriasis, diabetes, multiple sclerosis, cancer and chronic obstructive pulmonary disease.

The present invention further concerns a process for preparing the compounds of the invention, their salts, hydrates or solvates.

The compounds of formula (I) can be obtained according to following method.

Step (1): The diacyl chloride, bromide, fluoride or di-activated ester of fumaric acid or the monoacyl chloride, bromide, fluoride or mono-activated ester of a mono-ester, mono-amide or mono-thioester of fumaric acid is esterified with a compound of formula (X) chosen from among:
wherein Z and Q are as defined above.

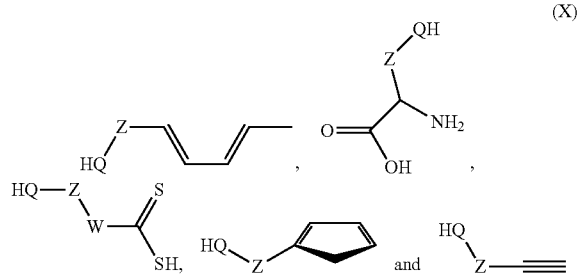

Alternatively, fumaric acid or the mono-ester of fumaric acid may be alkylated with a compound of formula (XI) chosen from among:

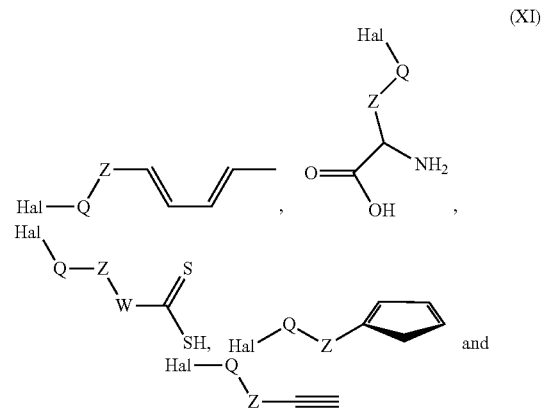

wherein Z and Q are as defined above and Hal represents a leaving group such as halogen or sulfonate, such as trifluoromethane-sulfonate.

Step (2): the compound obtained in step (1) is reacted with a suitable carbonyl metal complex of formula $L_1L_2M_x(CO)_y$, where x is 1 or 2 and y is 1 to 10, $L_1$ and $L_2$ represent each a monodentate ligand or $L_1L_2$ represents a bidentate ligand to yield after optional deprotection the compound of formula (I).

The invention therefore concerns a process for the synthesis of a compound of formula (I) comprising the reaction of a caffeic acid derivative of formula (XII):

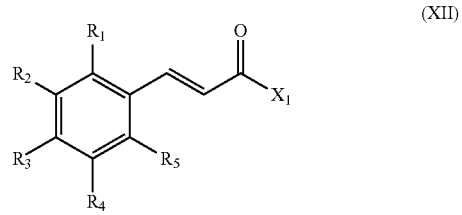

wherein:
$X_1$ represents $A-R_{21}$, A-CORM, A'-CORM' or Q'-Y as defined for formula (I), and
$R_{21}$ represents a group chosen from among:

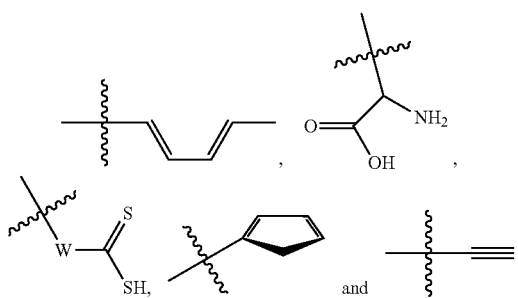

with a carbonyl metal complex of formula $L_1L_2M_x(CO)_y$ where x is 1 or 2 and y is 1 to 10, $L_1$ and $L_2$ represent each a monodentate ligand or $L_1L_2$ represents a bidentate ligand.

The invention also concerns a process for the synthesis of a compound of formula (II) comprising the reaction of a heterocycle containing compound of formula (XIII):

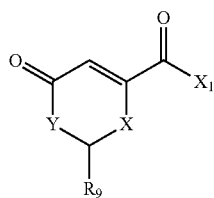

(XIII)

wherein:

X₁ represents A-R$_{21}$, A-CORM, as defined for formula (I), and

R$_{21}$ represents a group chosen from among:

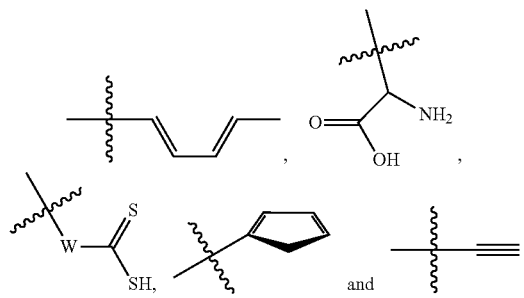

with a carbonyl metal complex of formula $L_1L_2M_x(CO)_y$, where x is 1 or 2 and y is 1 to 10, $L_1$ and $L_2$ represent each a monodentate ligand or $L_1L_2$ represents a bidentate ligand.

DESCRIPTION OF THE FIGURES

FIG. 4A represents HO-1 protein expression measured in H9c2 cardiomyocytes cultured at 20% (upper panel) or 5% (lower panel) oxygen (O₂) 6 h after treatment with increasing concentrations (1 µM to 10 µM) of hybrids, more particularly compound C; HO-1 protein expression measured in H9c2 cardiomyocytes cultured at 20% (upper panel) or 5% (lower panel) oxygen (O₂) 24 h after treatment with increasing concentrations (1 µM to 10 µM) of hybrids, more particularly compound C (FIG. 4B); FIG. 4A and FIG. 4B represent the densitometric analysis of 3 independent Western blots for HO-1.

Figure 1:
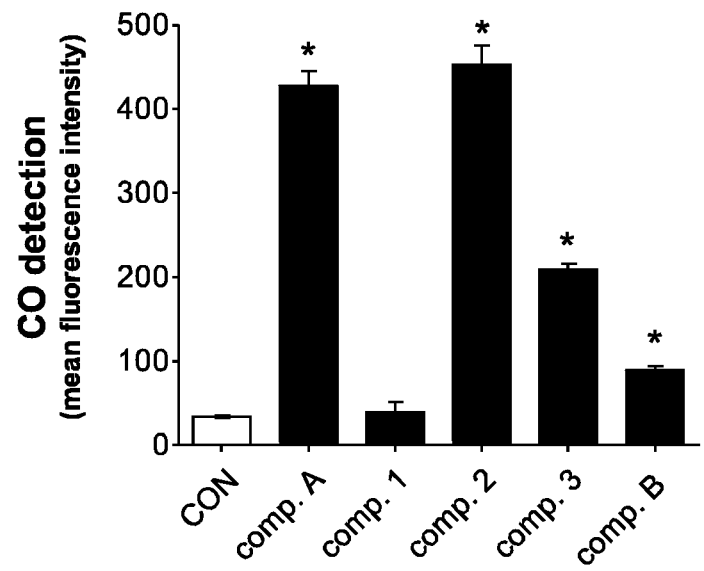
FIG. 1 represents the in vitro CO release by hybrids as measured by fluorescence spectra 60 min after addition of the hybrids to a buffer containing a CO-sensitive fluorescent probe (COP-1) (FIG. 1A), or after addition of hybrids to human THP-1 cells loaded with COP-1 (FIG. 1B).
Figure 1:
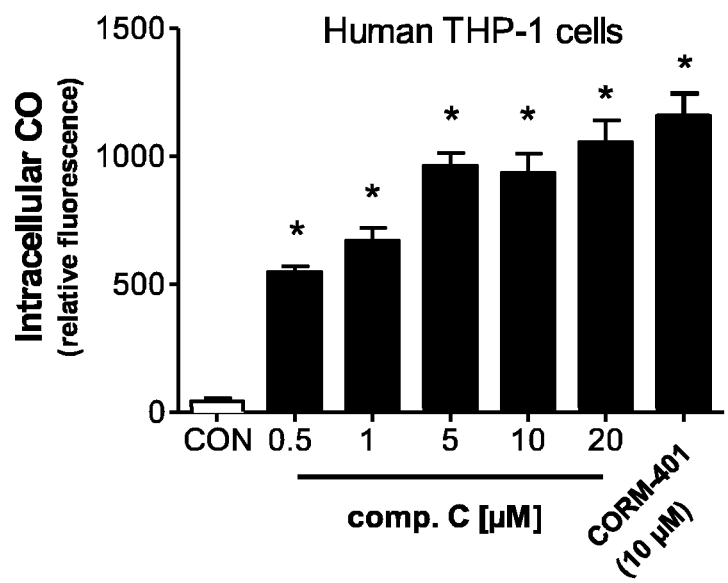

The present invention is illustrated by the non-limiting following examples.

Example 1: Synthesis of Hybrids
Chromone-CO-RM According to the Invention

Compound A:

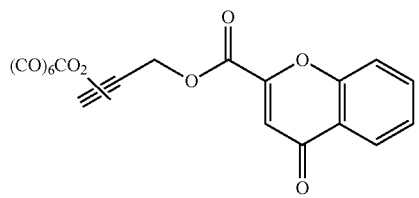

Step 1: Preparation of

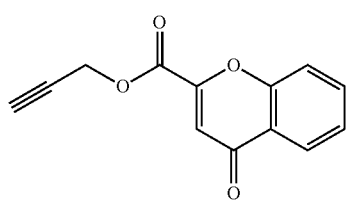

AO59

To a suspension of chromone-2-carboxylic acid (380 mg, 2.00 mmol, 1.0 equiv.) in acetonitrile (40 mL) were added under argon $K_2CO_3$ (332 mg, 2.40 mmol, 1.2 equiv.) and propargyl bromide solution (80 wt. % in toluene) (557 µL, 5.00 mmol, 2.5 equiv.). After 17 h of stirring at 50° C., the reaction mixture was concentrated in vacuo, then, dissolved in diethyl ether, filtered on celite and concentrated in vacuo. The resulting crude product was purified by silica gel column chromatography eluting with cyclohexane/EtOAc (75/25) to afford AO59 (157 mg, 0.69 mmol) as a white solid in 35% yield. $^1$H NMR (400 MHz, $CDCl_3$) δ 8.20 (dd, J=8.0, 1.5 Hz, 1H), 7.75 (ddd, J=8.7, 7.2, 1.7 Hz, 1H), 7.62 (d, J=8.5 Hz, 1H), 7.46 (m, 1H), 7.17 (s, 1H), 4.99 (d, J=2.5 Hz, 2H), 2.60 (t, J=2.5 Hz, 1H). $^{13}$C NMR (100 MHz, $CDCl_3$) δ 178.18, 159.90, 155.94, 151.37, 134.86, 126.03, 125.78, 124.44, 118.78, 115.41, 76.40, 76.13, 54.05. Anal. Calcd for $C_{13}H_8O_4$ (228.20): C, 68.42; H, 3.53; 0, 28.04. Found: C, 68.36; H, 3.71; 0, 27.87.

Step 2: Preparation of Compound A

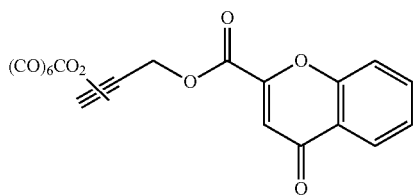

To a degassed solution of AO59 (157 mg, 0.69 mmol, 1.0 equiv.) in $CHCl_3$ (10 mL) was added dicobalt octacarbonyl (283 mg, 0.83 mmol, 1.2 equiv.). After 16 h of stirring at 20° C. and 6 h of stirring at 40° C., the reaction mixture was concentrated in vacuo. The resulting crude product was purified by silica gel column chromatography eluting with cyclohexane/EtOAc (90/10) to afford compound A (252 mg, 0.49 mmol) as a dark red solid in 71% yield. $^1$H NMR (400 MHz, $C_6D_6$) δ 8.22 (d, J=7.5 Hz, 1H), 7.19 (m, 1H), 7.13 (m, 1H), 6.96 (t, J=7.2 Hz, 1H), 6.79 (t, J=7.1 Hz, 1H), 5.33 (s, 1H), 4.98 (s, 2H). $^{13}$C NMR (100 MHz, $C_6D_6$) δ 199.25, 177.22, 160.38, 156.12, 151.64, 134.31, 126.08, 125.79, 125.11, 118.51, 115.59, 87.65, 72.08, 66.86. Anal. Calcd for $C_{19}H_8Co_2O_{10}$ (514.13): C, 44.39; H, 1.57. Found: C, 44.49; H, 1.57.

Example 2: Synthesis of Hybrids Caffeic Acid-CO-RM According to the Invention

Compound B:

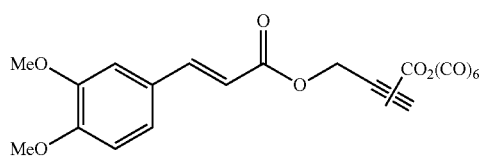

Step 1: Preparation of

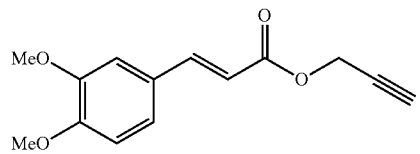

To a solution of 3,4-dimethoxycinnamic acid (208 mg, 1.00 mmol, 1.0 equiv.) in acetonitrile (17 mL) were added, at 20° C. and under argon, potassium carbonate (152 mg, 1.10 mmol, 1.1 equiv.) and propargyl bromide solution (80 wt. % in toluene) (123 µL, 1.10 mmol, 1.1 equiv.). After 17 h of stirring at 70° C., the reaction mixture is filtered and concentrated in vacuo. The crude is dissolved in $Et_2O$/$NaHCO_3$ (sat) and the aqueous layer is extracted by $Et_2O$. The resulting organic layers are washed with brine, dried on $MgSO_4$, filtered and concentrated in vacuo. This resulting crude product was purified by flash silica gel column chromatography eluting with cyclohexane/EtOAc (80/20) to afford AO281 (214 mg, 0.87 mmol) as a white solid in 87% yield. $^1$H NMR (400 MHz, $CDCl_3$) δ 7.68 (d, J=15.9 Hz, 1H), 7.11 (dd, J=8.3, 2.0 Hz, 1H), 7.05 (d, J=1.9 Hz, 1H), 6.87 (d, J=8.3 Hz, 1H), 6.33 (d, J=15.9 Hz, 1H), 4.81 (d, J=2.4 Hz, 2H), 3.91 (d, J=2.2 Hz, 6H), 2.51 (t, J=2.4 Hz, 1H). $^{13}$C NMR (100 MHz, $CDCl_3$) δ 166.26, 151.31, 149.17, 145.86, 127.09, 122.86, 114.57, 110.96, 109.53, 77.85, 74.81, 55.95, 55.84, 51.92. Anal. Calcd for $C_{20}H_{14}Co_2O_{10}$ (532.19): C, 45.14; H, 2.65. Found: C, 45.18; H, 2.66.

Step 2: Preparation of Compound B

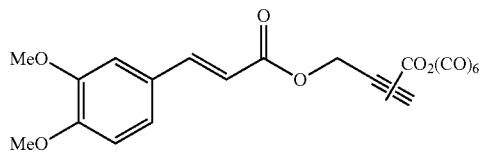

To a degassed solution of AO281 (239 mg, 0.97 mmol, 1.0 equiv.) in $CHCl_3$ (10 mL) was added dicobalt octacarbonyl (332 mg, 0.97 mmol, 1.0 equiv.). After 5 h30 of stirring at 20° C., the reaction mixture was concentrated in vacuo. The resulting crude product was purified by silica gel column chromatography eluting with cyclohexane/EtOAc (80/20) to afford comp. B (464 mg, 0.87 mmol) as a dark red powder in 90% yield. $^1$H NMR (400 MHz, $C_6D_6$) δ 8.03 (d, J=15.4 Hz, 1H), 6.87 (d, J=6.6 Hz, 1H), 6.79 (s, 1H), 6.59 (d, J=15.7 Hz, 1H), 6.34 (d, J=7.0 Hz, 1H), 5.41 (s, 1H), 5.20 (s, 2H), 3.26 (s, 6H). $^{13}$C NMR (100 MHz, $C_6D_6$) δ 199.63, 166.57, 152.37, 150.27, 146.36, 122.81, 115.07, 111.71, 110.64, 90.55, 71.98, 64.33, 55.33, 55.26. Anal. Calcd for $C_{20}H_{14}Co_2O_{10}$ (532.19): C, 45.14; H, 2.65. Found: C, 45.18; H, 2.66.

Compound C:

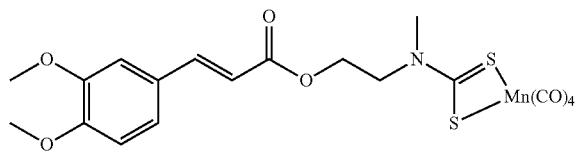

Step 1: Preparation of Sodium (2-hydroxyethyl)(methyl)carbamodithioate

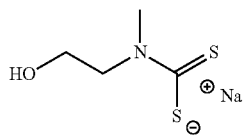

To a solution of carbon disulfide (452 µL, 7.50 mmol, 1.5 equiv.) in anhydrous tetrahydrofuran (10 mL) was added, at 0° C. under argon and dropwise, 2-(methylamino)ethanol (400 µL, 5.00 mmol, 1.0 equiv.). After 5 min of stirring at 0° C., sodium hydride (60% dispersion in mineral oil) (200 mg, 5.00 mmol, 1.0 equiv.) was added portionwise. After 30 min of stirring at 0° C., the reaction mixture was concentrated in vacuo. The resulting crude product was washed several time with cyclohexane to eliminate mineral oil and then concentrated in vacuo et dried with a vane pump during one night to afford AO45 (842 mg, 4.9 mmol) as a pale yellow powder in 97% yield which was used in the next step without further purification. $^1$H NMR (400 MHz, MeOD) δ 4.27 (t, J=6.0 Hz, 2H, CH$_2$O), 3.87 (t, J=6.0 Hz, 2H, CH$_2$N), 3.57 (s, 3H, CH$_3$N). $^{13}$C NMR (100 MHz, MeOD) δ 213.99 (CS$_2$), 61.14 (CH$_2$O), 59.07 (CH$_2$N), 44.65 (CH$_3$N). C$_4$H$_8$NNaOS$_2$. M=173.23.

Step 2: Preparation of AO45

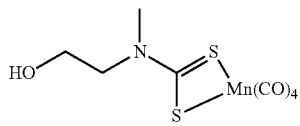

To a degassed solution of Mn(CO)$_5$Br (137 mg, 0.50 mmol, 1.0 equiv.) in methanol (8 mL) was added AO45 (87 mg, 0.50 mmol, 1.0 equiv.). After 3 h30 of stirring at 45° C. under argon, the reaction mixture was concentrated in vacuo, dissolved in diethyl ether, filtered on celite and concentrated in vacuo to afford AO55 (149 mg, 0.47 mmol) as a yellow oil in 94% yield which was used in the next step without further purification. $^1$H NMR (400 MHz, MeOD) δ 3.87 (t, J=5.3 Hz, 2H, CH$_2$O), 3.80 (t, J=5.2 Hz, 2H, CH$_2$N), 3.33 (s, 3H, CH$_3$N). $^{13}$C NMR (100 MHz, MeOD) δ 209.23 (CO$_{metal}$), 188.25 (CS$_2$), 59.94 (CH$_2$N), 54.65 (CH$_2$O), 38.74 (CH$_3$N). $^{55}$Mn NMR (100 MHz, MeOD) δ—1035.4. Anal. Calcd for C$_8$H$_8$MnNO$_5$S$_2$ (317.22): C, 30.29; H, 2.54; N, 4.42. Found: C, 30.50; H, 2.54; N, 4.23.

Step 3: Preparation of Compound AO277

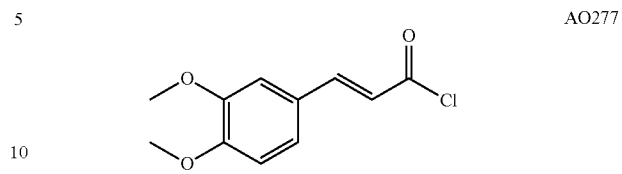

To a suspension of 3,4-dimethoxycinnamic acid (625 mg, 3.00 mmol, 1.0 equiv.) in CH$_2$Cl$_2$ (5 mL) were added, under argon at 0° C., oxalyl chloride (652 µL, 7.50 mmol, 2.5 equiv.) and a catalytic amount of DMF (2 drops). After 3 h of stirring at 20° C. under argon, the reaction mixture was concentrated in vacuo to afford quantitatively AO277 (680 mg, 3.00 mmol) which was used in the next step without further purification. $^1$H NMR (400 MHz, acetone d$^6$) δ 7.88 (d, J=15.4 Hz, 1H), 7.48 (d, J=2.0 Hz, 1H), 7.39 (dd, J=8.4, 2.0 Hz, 1H), 7.07 (d, J=8.3 Hz, 1H), 6.79 (d, J=15.4 Hz, 1H), 3.90 (s, 3H), 3.90 (s, 3H). $^{13}$C NMR (100 MHz, acetone d$^6$) δ 166.05, 154.28, 152.67, 150.77, 126.94, 126.22, 119.87, 112.33, 111.66, 56.20.

Step 4: Preparation of Compound C

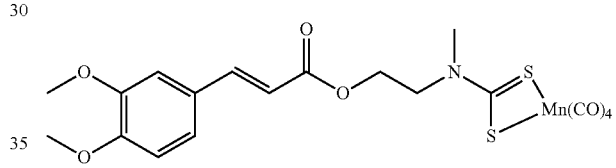

To a solution of AO55 (476 mg, 1.50 mmol, 1.0 equiv.) in anhydrous and degassed CH$_2$Cl$_2$ (10 mL) were added a solution of AO277 (680 mg, 3.00 mmol, 2.0 equiv.) in anhydrous and degassed CH$_2$Cl$_2$ (10 mL) and then 4-DMAP (330 mg, 2.70 mmol, 1.8 equiv). After 17 h of stirring at 40° C. under argon, the reaction mixture was concentrated in vacuo. The resulting crude product was purified by silica gel column chromatography eluting with cyclohexane/EtOAc (70/30) and dried with a vane pump during one night to afford AO280 (444 mg, 0.88 mmol) as a yellow powder in 59% yield. $^1$H NMR (400 MHz, C$_6$D$_6$) δ 7.93 (d, J=14.8 Hz, 1H), 6.85 (d, J=6.4 Hz, 1H), 6.80 (s, 1H), 6.42 (d, J=16.2 Hz, 1H), 6.38 (d, J=8.4 Hz, 1H), 3.94 (s, 2H), 3.31 (s, 2H), 3.26 (s, 6H), 2.50 (s, 3H). $^{13}$C NMR (100 MHz, C$_6$D$_6$) δ 209.62, 204.14, 166.57, 152.45, 150.29, 146.45, 127.39, 123.02, 114.87, 111.63, 110.51, 59.83, 55.33, 49.74, 36.58. $^{55}$Mn NMR (100 MHz, C$_6$D$_6$) δ—971.6. Anal. Calcd for C$_{19}$H$_{18}$MnNO$_8$S$_2$ (507.42): C, 44.97; H, 3.58; N, 2.76. Found: C, 45.24; H, 3.83; N, 2.60.

Comparatives compounds are:

HYCO1:

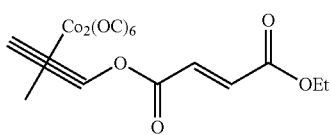

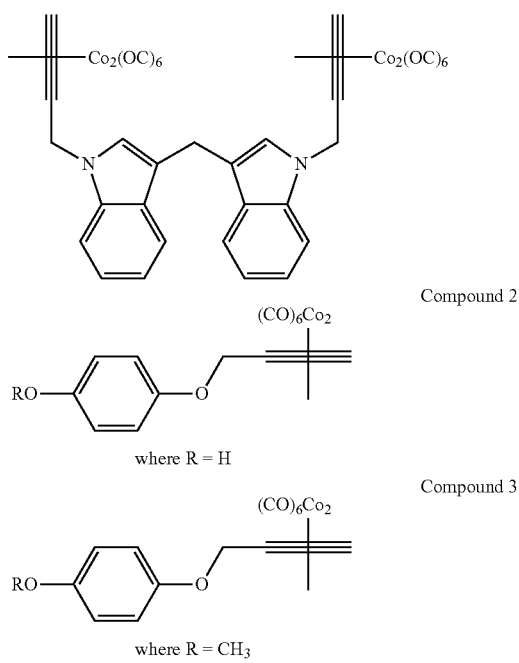

Compound 1

Compound 2
where R = H

Compound 3
where R = CH$_3$

Example 3: Assessment of CO-Release by Compounds of the Invention

Assessment of CO-Release in COP-1 Fluorescence Assay by Compounds a, B and C:

The release of CO from hybrids was assessed using COP-1, a fluorescent probe sensitive to CO. The fluorescence intensity of COP-1 (2 µM, Δex=475 nm) in buffer was measured in a cuvette to obtain a background fluorescence spectrum and spectra were then recorded immediately after addition of 50 µM tested compounds. The mean fluorescence intensity (MFI) of 3 independent reading was calculated using the fluorescence intensity values recorded at 507 nm after 60 min.

The results are presented in FIG. 1.

As shown by these results, all compounds of the invention release carbon monoxide whereas the curcumin derivative according to WO 2012/076696 (data not shown) and the compound 1, diindolylmethane derivative, do not.

From the measurements shown in FIG. 1A, all compounds with the exception of diindolylmethane derivative liberated CO, albeit in different amounts. Compound A and compound 2 release the highest amount of CO, compound 3 exhibits intermediate release while compound B liberates the smallest amount of CO (FIG. 1A).

To detect whether the compounds delivered CO to cells, human THP-1 cells were initially suspended in Dulbecco Phosphate Buffer Solution (+Ca, +Mg; Gibco® Cell Culture, Life Technologies) and then treated with compounds at a concentration of 10 µM for 15 min at 37° C. in 5 ml polypropylene round-bottom tubes (BD Falcon, Dominique Dutscher). Cells were then incubated for 30 min with 1 µM COP-1. Intracellular fluorescence of COP-1 was measured using a CyAnTM ADP LX7 Analyzer (Beckman Coulter) as previously reported.

The results indicate that compound C, which shares a similar structure with compound B liberates a significant and high amount of CO when incubated with human THP-1 cells (FIG. 1B).

Hence, caffeic acid hybrids according to the invention are able, despite a low release in buffer, to induce a significant CO release in presence of human cells which is comparable with previously described CORM-401.

Figure 2:
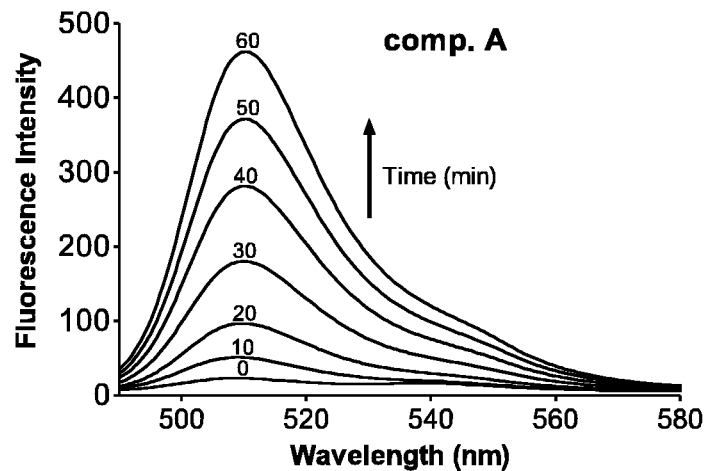
FIG. 2 represents the in vitro CO release from compounds of the invention compared to HYCO-1.
Figure 2:
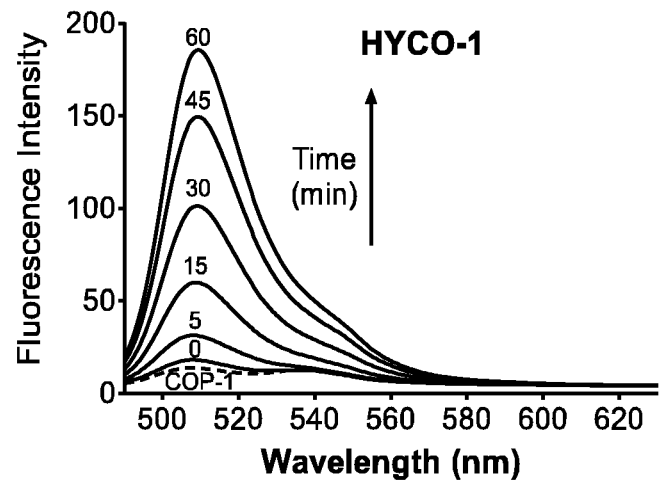

Analysis of the release rate of CO shows that compounds of the invention have a faster release rate of CO compared to previously disclosed HYCO-1 (FIGS. 2B and 2C).

Moreover, compound A shows at 60 minutes more than twice the amount of CO released as compared to HYCO-1.

Example 4: In Vitro Assessment of the Biological Activity of Compounds A and B

Example 4.1: Assessment of Nuclear Expression of Nrf2 and HO-1 Activation after Exposure of BV2 Microglia Cells to Compounds A and B Cells were grown in an atmosphere of 5% CO$_2$ at 37° C. in either 75 cm$^2$ flasks, 100 mm diameter Petri dishes, 6- or 24-well plates containing medium supplemented with 10% fetal bovine serum (Lonza) and penicillin (100 U·mL$^{-1}$)/streptomycin (100 mg·mL$^{-1}$; Life Technologies). BV2 mouse microglial cells were grown in RPMI-1640 containing 2 g·L$^{-1}$ glucose and supplemented with 0.3 g·L$^{-1}$ 1-glutamine.

BV2 microglia were incubated with 10 µM of hybrids for 2 h to assess nuclear translocation of Nrf2. Nuclear fractions were isolated using a Nuclear Extract Kit from Active Motif (La Hulpe, Belgium), according to the manufacturer's instructions, and stored at −80° C. Protein concentrations were measured using a Pierce BCA Protein Assay kit (Thermo Scientific).

To determine HO-1 protein expression, BV2 microglia were incubated with 10 µM hybrids (compounds) for 6 h. At the end of the incubation cells were washed with ice cold DPBS (—Ca, —Mg; Gibco® Cell Culture, Life Technologies) and lysed during 30 min incubation at 4° C. in cell lysis buffer (50 mM HEPES, 150 mM NaCl, 50 mM NaF, 50 µM Na$_3$VO$_4$, 1% v/v Triton X-100 and 1% mammalian protease inhibitor). Lysates were centrifuged for 10 min at 15,000×g and 4° C.; supernatants were collected and stored at −80° C. Protein concentrations were measured using a Pierce BCA Protein Assay kit (Thermo Scientific).

Whole cell lysates (20 µg protein/sample) were resolved on 12% acrylamide gels, respectively, and proteins transferred to polyvinylidene difluroride membranes (Millipore, Brussels, Belgium). Membranes were blocked for 1 h at room temperature in 1× Tris-buffered saline (pH 7.5) containing 0.1% v/v TWEEN 20 and 5% w/v non-fat dry milk and incubated overnight at 4° C. with the following primary antibodies: HO-1 (rabbit polyclonal, Enzo Life Sciences) and β-actin (clone 8H$_{10}$D$_{10}$, mouse monoclonal, Cell Signaling Technology) as a loading control. Membranes were then incubated with secondary antibodies coupled to horseradish peroxidase (goat anti-mouse or anti-rabbit, Cell Signaling Technology or donkey anti-goat, Jackson ImmunoResearch) for 1 h at room temperature. Bands were detected with chemiluminescent substrates (Pierce ECL®, Thermo Scientific or RevelBIOt® Intense, Ozyme) and images captured using a G:Box F3 Imagery Station and GeneSys Software (Syngene, Cambridge, UK). To determine Nuclear expression of Nrf2 protein, nuclear extracts (50 µg protein/sample) and whole cell lysates (20 µg protein/sample) were resolved on 10 or 12% acrylamide gels, respectively, and proteins transferred to polyvinylidene difluroride membranes (Millipore, Brussels, Belgium). Membranes were blocked for 1 h at room temperature in 1× Tris-buffered saline (pH 7.5) containing 0.1% v/v TWEEN 20 and 5% w/v non-fat dry milk and incubated overnight at 4° C. with the following primary antibody for Nrf2: clone C-20 rabbit polyclonal, Santa Cruz Biotechnology). Membranes were then incubated with secondary antibodies coupled to horse-radish peroxidase (goat anti-mouse or anti-rabbit, Cell Signaling Technology or donkey anti-goat, Jackson ImmunoResearch) for 1 h at room temperature. Bands were detected with chemiluminescent substrates (Pierce ECL®, Thermo Scientific or RevelBlOt® Intense, Ozyme) and images captured using a G:Box F3 Imagery Station and GeneSys Software (Syngene, Cambridge, UK).

Figure 3:
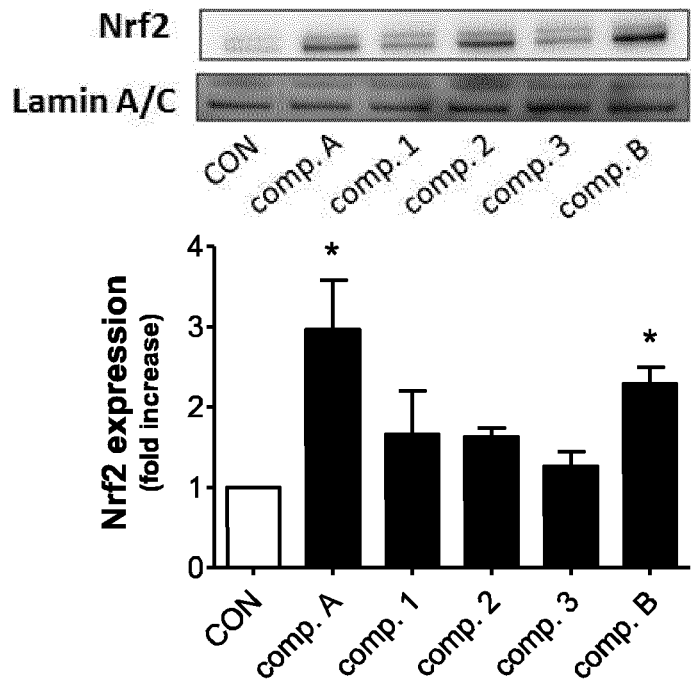
FIG. 3 represents nuclear expression of Nrf2 2 h after exposure of BV2 cells to 10 µM of hybrids (FIG. 3A); HO-1 protein expression measured in BV2 cells 6 h after treatment with 10 µM of hybrids (FIG. 3B). The lower panels in (A) and (B) represent the densitometric analysis of 3 independent Western blots for Nrf2 and HO-1, respectively.
Figure 3:
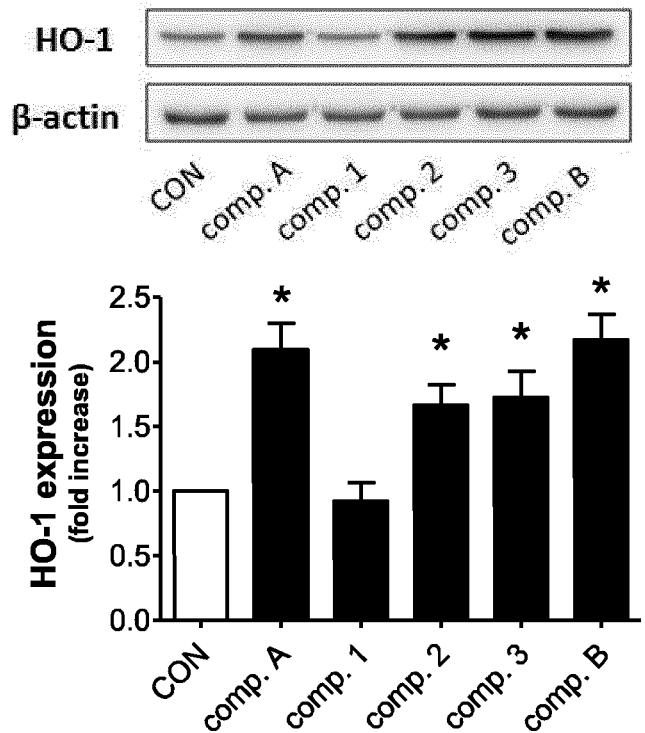

The results are presented in FIG. 3A-B.

Exposure of BV2 microglia cells to 10 μM of compound A and compound B for 2 h strongly promoted the accumulation of Nrf2 in the nucleus.

In addition, after 6 h of treatment, compound A and compound B induced a two-fold increase in HO-1 protein expression.

In comparison, compounds 1, 2 and 3 were less effectives both as an Nrf2 activator and HO-1 inducing agent.

Example 4.2: Assessment of HO-1 Activation after Exposure of H9c2 to Compound C The assessment of HO-1 induction by western blotting was performed as previously (Example 4.1). H$_9$C2 cells rat cardiomyocytes were cultured in Dubelcco's Modified Eagle Medium containing: glucose 4.5 g/l, L-glutamine 2 mM, pyruvate) supplemented with fetal bovine serum (FBS) 10%, a mixture of penicillin (10,000 IU/ml)/streptomycin (10 mg/ml) (Gibco Life Technologies) and sodium Pyruvate 1% (Gibco Life Technologies). Cells were grown and subcutlured either in a normal incubator at 20% $O_2$ or in a dedicated chamber in which the $O_2$ levels was kept constantly at 5%, a value which reflects more closely the $O_2$ concentrations found in vivo. For the adaptation of cells at 5 $O_2$, cells were grown and passaged at least twice before conducting any experiment.

Figure 4:
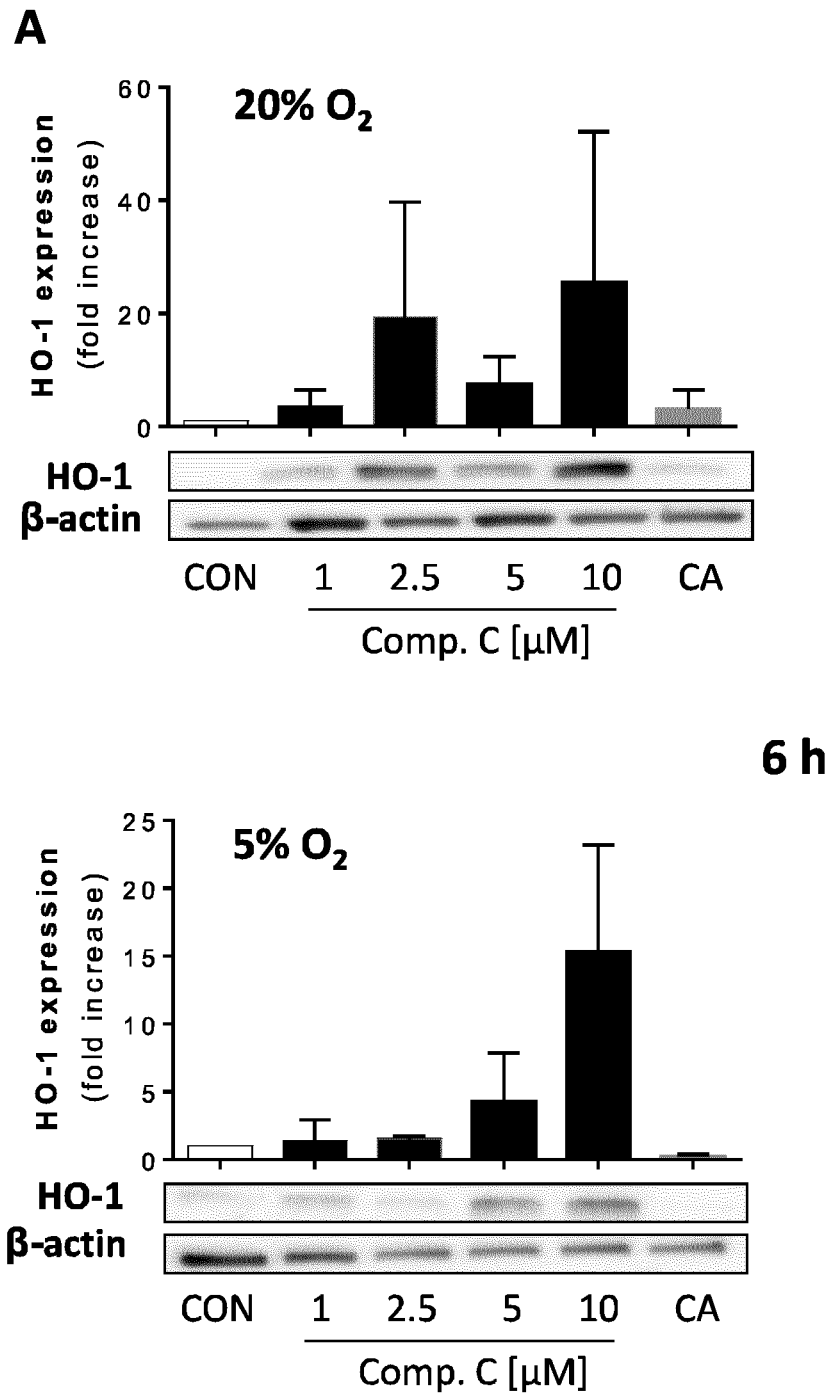
Figure 4:
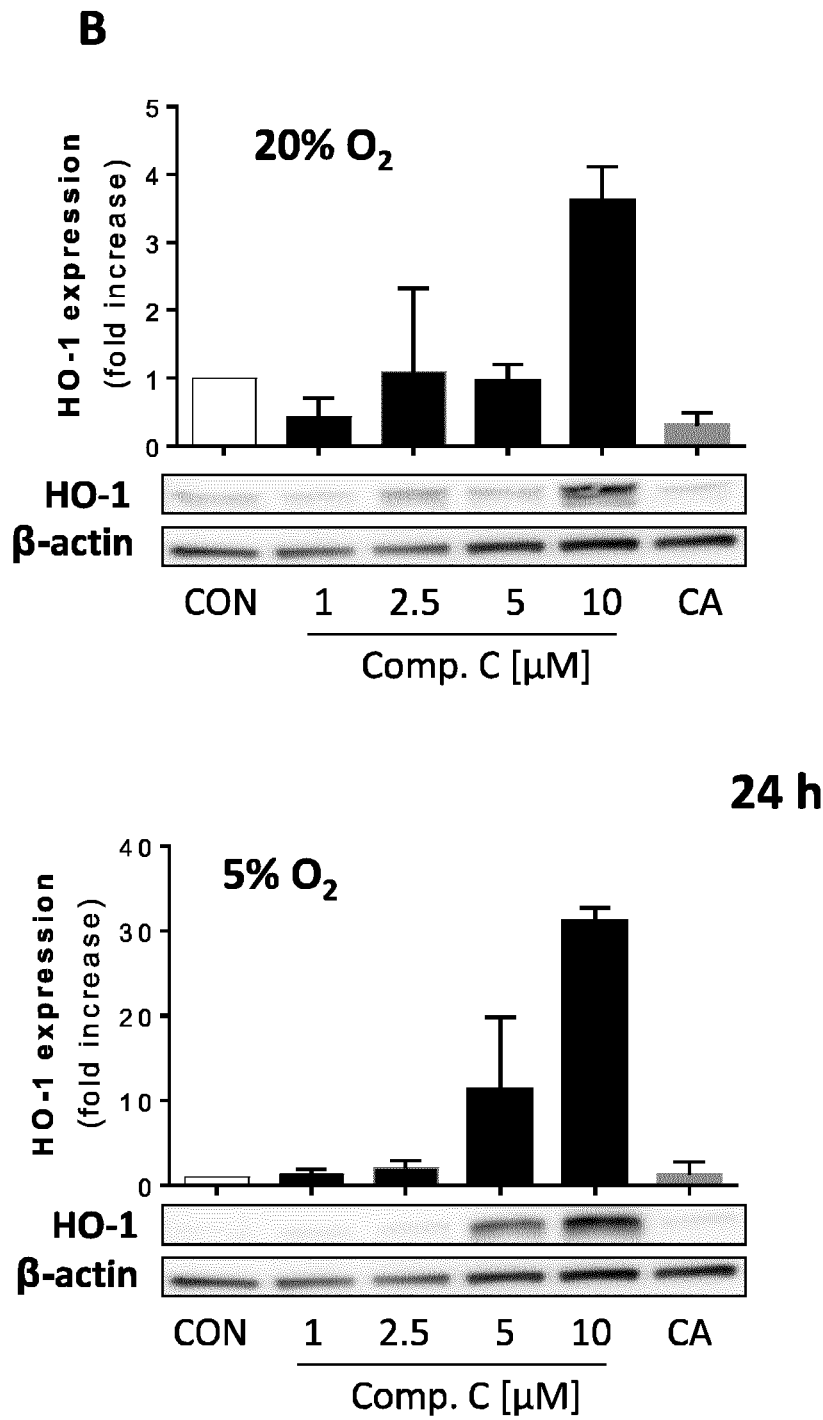

H9c2 cardiomyocytes were then incubated with increasing concentration of compound C (1 μM to 10 μM) for 6 h or 24 h either at 20% or 5% $O_2$. The results are presented in FIG. 4A-4B. Exposure of H9c2 cardiomyocytes to increasing concentrations of compound C induced an increase in HO-1 protein expression for the different concentration of compound C.

In addition, compound C is capable of inducing a significant expression of HO-1 both at 20% and 5% 02. CA=dimethoxy cinnamic acid (Nrf2 inducing moiety present in compound C).

Example 4.3: Assessment of Nrf2 and HO-1 Activation after Exposure of Human THP-1 Cells to Compound C Human monocytes (THP-1 cells) were cultured in RPMI 1640-Glutamax medium supplemented with 1% penicillin/streptomycin, 1% sodium pyruvate and 10% fetal bovine serum (RPMIc). Cells at confluence were washed with PBS and treated with compound C at different concentrations for 6 h according to the experimental protocol. Compound C was dissolved in DMSO at 0.1% as a final concentration in complete medium.

Figure 5:
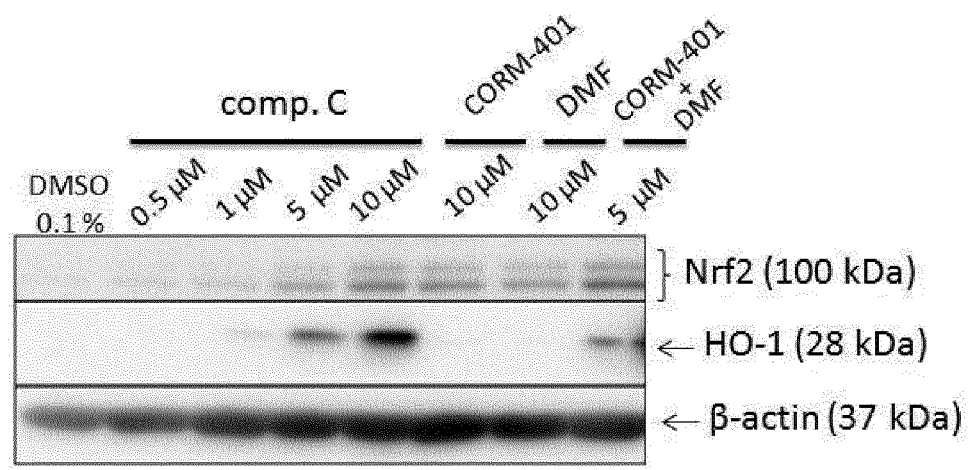
FIG. 5 represents the effect of compound C compared to DMF or CORM-401 alone or a combination of DMF+CORM-401 on the expression of Nrf2 measured 6 h after exposure of human THP-1 cells to increasing concentration of compound C and HO-1 protein expression measured in human THP-1 cells 6 h after treatment with increasing concentration of compound C.

As for BV2 microglia cells, exposure of THP-1 cells to compound C strongly promoted the activation of Nrf2 and induction of HO-1 protein expression (FIG. 5).

Furthermore, when compared with HO-1 activation with comparative compounds CORM-401 and DMF, compound C induced a concentration-dependent increase in HO-1 protein expression starting from 1 μM of compound C, whereas 10 fold this concentration is not sufficient for the detection of an increase of HO-1 protein expression with comparative compounds CORM 401 and DMF.

Beside, a combination of CORM 401 and DMF have been tested by the inventors and show for the first time a synergistic action of those two compounds for the increase of HO-1 protein expression. Although it is shown the benefit of using a combination of an HO-1 or Nrf2 inducer with a CORM, compounds of the invention are still more potent than this combination.

Example 4.4: Assessment of Reduced Glutathione after Exposure of Cells to Compounds A and B The 5,5' dithiobis-(2-nitrobenzoic acid) (DTNB) colorimetric assay was used for the measurement of reduced glutathione (GSH). Briefly, BV2 microglia cells were seeded in 6-well-plates and incubated with 10 μM hybrids and dimethyl fumarate (DMF, positive control) for 3, 6 and 24 h. At the end of the incubation period, cells were initially washed with phosphate buffers solution, then scraped in 600 μL of 2% (w/v) 5-sulposalicylic acid solution and transferred to a 1.5 ml microtube, and finally centrifuged for 5 min at 10,000×g. An aliquot of the supernatant (500 μl) was then reacted with 0.5 ml DTNB solution (0.3 M sodium phosphate buffer, 10 mM EDTA and 0.2 mM DTNB) and after 5 min the absorbance was read spectrophotometrically at 412 nm (extinction coefficient 14.3 mM$^{-1}$ cm$^{-1}$).

Figure 6:
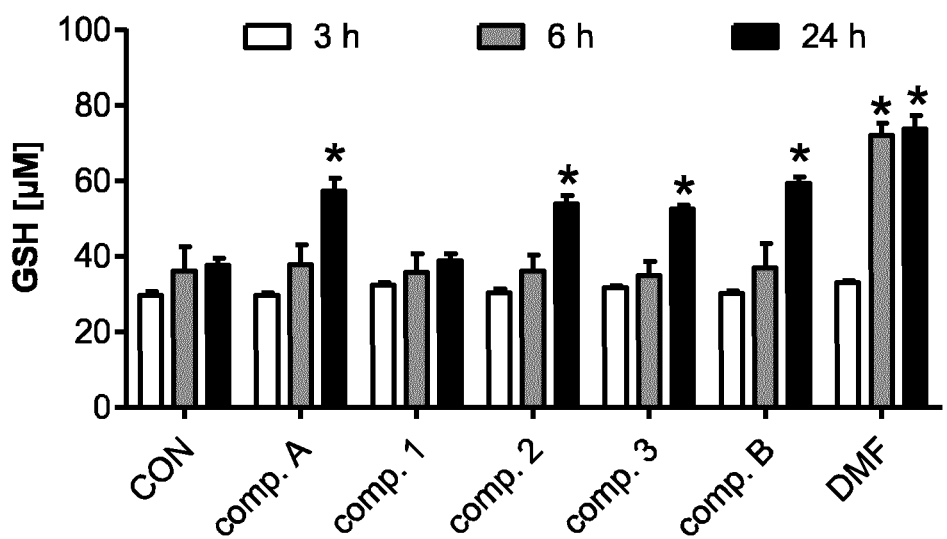
FIG. 6 represents intracellular reduced glutathione (GSH) measured at 3, 6 and 24 h after exposure of BV2 cells to 10 µM of hybrids and DMF (n=3 independent experiments).

Whereas DMF raised the level of GSH from 6 h of treatment, all hybrids tested, excluding compound 1, did not change GSH at 3 or 6 h (FIG. 6). Hence, compound of the invention, including compound A and compound B show no side effect concerning glutathione reduction. Furthermore, the significant raise at 24 h after treatment observed for compound A and B, like that observed for DMF, is a positive outcome since GSH is a powerful intracellular antioxidant.

Example 5: In Vitro Assessment of the Anti-Inflammatory Activity of Compounds of the Invention

Example 5.1: Assessment of Nitrite Production after Exposure of Cells to Compounds A and B Nitrite production, an index of inflammation, was measured in BV2 cells challenged for 24 h with lipopolysaccharide (LPS, 1 μg/ml) in the presence or absence of increasing concentrations of hybrids. At the end of the incubation, nitrite levels were measured using the Griess method. Briefly, cell plates were centrifuged at 10,000×g for 5 min and the cell-free supernatant was incubated with an equal volume of Griess reagent (2 mM N-(1-naphtyl)ethyl-enediamide, 30 mM sulfanilamide and 140 mM o-phosphoric acid) for 10 min at room temperature. The absorbance was measured at 560 nm. Concentrations of nitrite (μM) were calculated from a standard curve of sodium nitrite.

Figure 7:
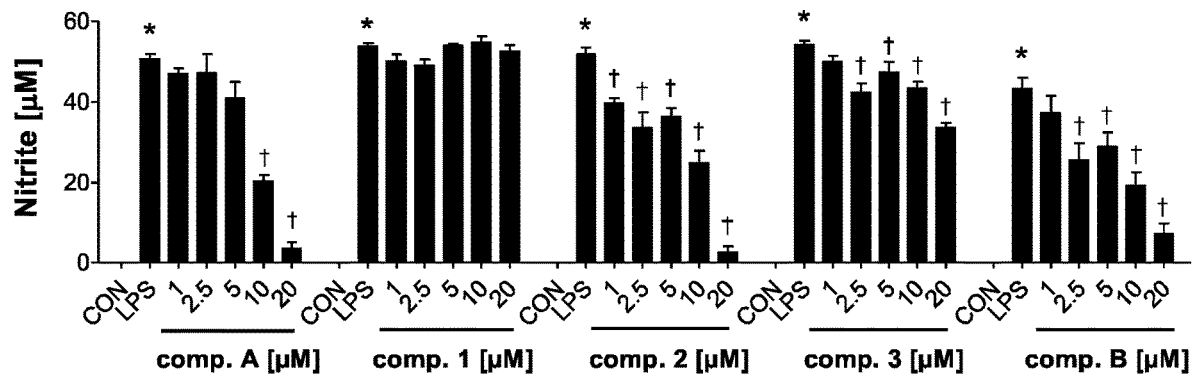
FIG. 7 represents on the Y axis nitrite production expressed in µM in BV2 microglia (CON), in BV2 microglia challenged for 24 h with lipopolysaccharide (LPS, 1 µg/ml) (LPS) and in BV2 microglia challenged with lipopolysaccharide (LPS, 1 µg/ml) (LPS) in the presence of increasing concentrations of hybrids.

The results are presented in FIG. 7.

Compounds A, B and 2 markedly decreased LPS-mediated nitrite accumulation, showing that the CORM group contributes to the reduction of nitrite levels. On the other side, compound 1 does not decrease nitrite level and compound 3 only show a low effect on nitrite concentration.

As evidenced by these results, compound A and B are significantly more active (by more than 4-fold) than the comparative compounds 1 and 3.

Example 5.2: Assessment of on IL-1β Production in Human THP-1 Cells Challenged with Lipopolysaccharide (LPS)

IL-1β production was measured in the supernatants of human THP-1 cells treated with LPS (100 µg/ml) in the presence or absence of 5 µM comp. C, DMF or CORM-401. After 24 h incubation, the medium was collected and IL-1β levels quantified using an ELISA kit (R&D Systems) following the manufacturer's instructions.

Figure 8:
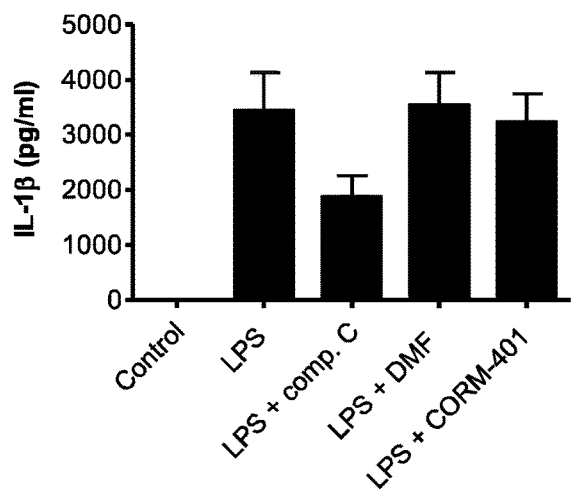
FIG. 8 represents the effect of compound C (5 µM) on IL-1β production in human THP-1 cells challenged with lipopolysaccharide (LPS) for 24 h.

The results are presented in FIG. 8.

Compound C decreased IL-1β production in human THP-1 cells whereas DMF or CORM-401 have no effect.

Such evidence confirms the anti-inflammatory potential of the compounds of the invention compared to previously described compounds.

Example 6: Assessment of the Cytotoxicity of Compounds of the Invention

Example 6.1: Assessment of the Cytotoxicity of Compound a and Compound B on BV2 Microglia Cytotoxicity was evaluated in BV2 microglia cells 24 h after incubation with increasing concentrations of hybrids using a Cytotoxicity Detection Kit (LDH) (Roche Applied Science) to measure lactate dehydrogenase released from damaged cells. X-100 Triton solution (2%) prepared in medium was used as a positive control (100% cytotoxicity). The assay was performed according to the manufacturer's instructions. Briefly, at the end of the incubation, cell plates were centrifuged at 300×g for 5 min and 100 µl cell-free supernatant transferred to a 96-well plate. A reaction mixture was added to the supernatant and the plate was incubated in the dark at room temperature with gentle shaking for 10 min. Absorbance was measured at 485 nm.

Data are expressed as percentage of LDH released by treating cells with 2% triton (100% toxicity).

Figure 9:
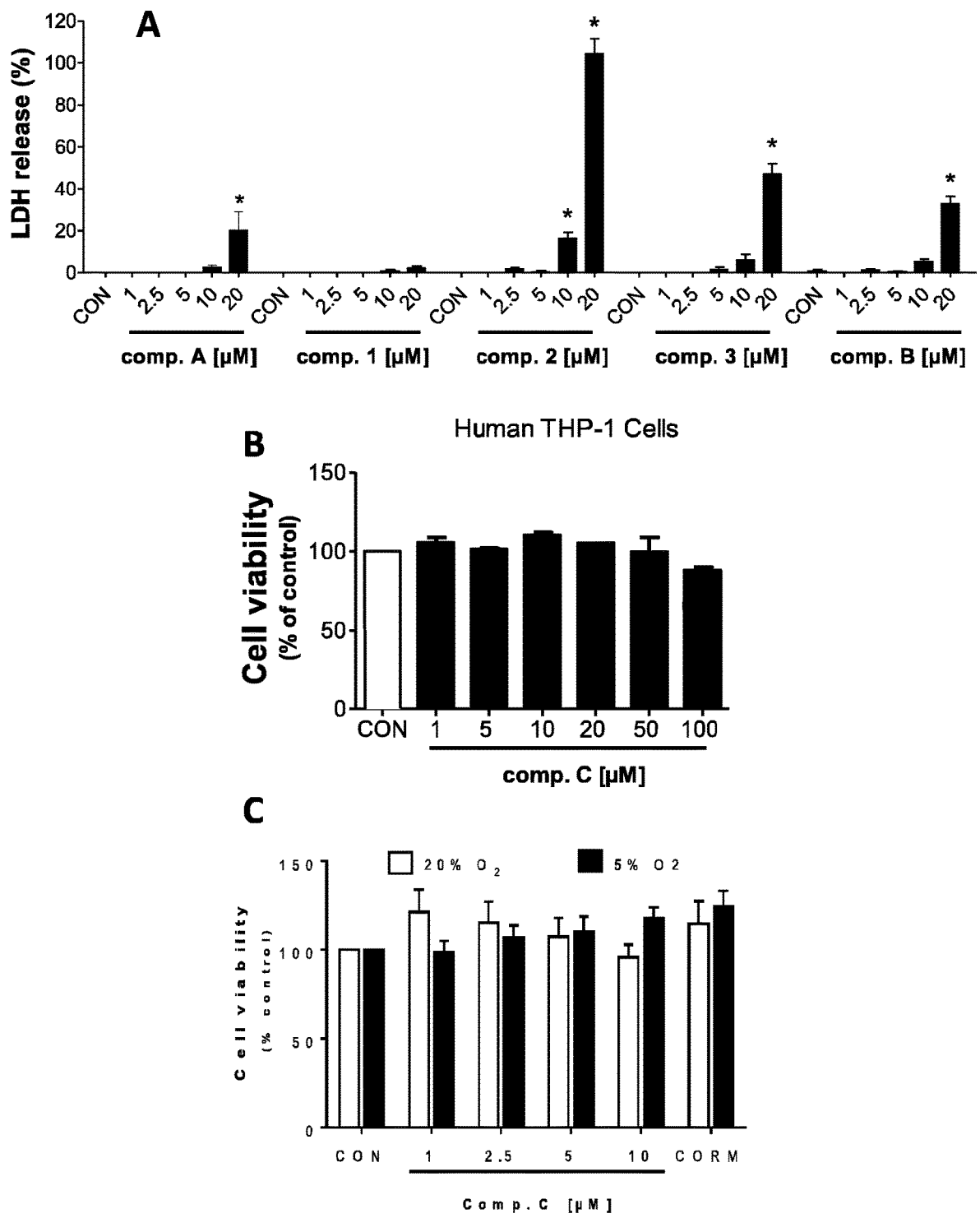
FIG. 9 represents the cytotoxicity of increasing concentration of hybrids in BV2 microglia measured by LDH release (FIG. 9A); the cytotoxicity of increasing concentration of compound B (X axis) in THP-1 cells (FIG. 9B) measured as percentage of control (Y axis) and the cytotoxicity of increasing concentration of compound C in H9c2 cardiomyocytes cultured at 20% or 5% oxygen for 24 h (FIG. 9C).

The results are presented in FIG. 9A.

Increasing concentrations of hybrids from 1 to 20 µM caused a variable release of lactate dehydrogenase (LDH), an index of cell injury, from BV2 cells exposed to the compounds for 24 h (FIG. 9A). At 20 µM comp. 1 was virtually without effect while comp. 2 promoted 100% toxicity. Twenty micromolar of compounds A, B and 3 increased cell toxicity to 20, 33, and 47% respectively whereas for 10 µM such compounds induce a LDH release lower than 10%.

Example 6.2: Assessment of the Effect of Compound C on Human THP-1 Cells and H9c2 Cardiomyocytes Viability Cytotoxicity was evaluated in THP-1 cells and H9c2 cardiomyocytes 24 h after incubation with increasing concentrations of compound C.

Human monocytes (THP-1 cells) were cultured in RPMI 1640-Glutamax medium supplemented with 1% penicillin/streptomycin, 1% sodium pyruvate and 10% fetal bovine serum (RPMIc). Cells at confluence were washed with PBS and treated with compound C at different concentrations and for different periods of time according to the experimental protocol. Compound C was dissolved in DMSO at 0.1% as a final concentration in complete medium.

H9c2 cardiomyocytes were cultured as previously (Example 4.2).

Cell viability was assessed using the previously described LDH assay.

The results are presented in FIGS. 9B and 9C.

Compound C do not show significant toxicity toward human THP-1 cells. Hence, compounds of the invention do not show a significant toxicity at concentration up to 10 µM.

In addition, compound C does not cause any visible toxic effect toward H9c2 cardiomyocytes at the concentrations used. CORM=CORM-401 (CO-releasing moiety present in compound C).

As shown in previous examples, at such concentrations, compounds A, B and C have good properties regarding: CO release, Nrf2 and HO-1 activation and anti-inflammatory potential. Thus, compounds A, B and C have been used in in vivo assay.

Example 7: Assessment of Tissue HO-1 Induction and Blood HbCO Levels In Vivo after Oral Administration of Compounds A, Compound B and Compound C Male C57 BL/6J mice were used for all experiments (Janvier Labs, France). Animals received at 8 weeks of age were placed on a standard diet and allowed to acclimatize for 2 weeks on a 12 hr light/dark cycle. All experiments were performed in compliance with INSERM guidelines for the use of animals and approved by the institutional review board at Paris-Est Creteil Val de Marne University. Mice were administered by oral gavage with a single dose of the following: 1) 200 µl of sesame oil (vehicle, control group); 2) Compound A (3 mg in 200 µl sesame oil); 3) Compound B (3 mg in 200 µl sesame oil).

Mice were sacrificed 6 hr after treatment by cervical dislocation. Livers, lungs, hearts and brains were excised and snap frozen for western blot analysis. Tissue samples were homogenized in lysis buffer (150 mM sodium chloride, 1.0% Triton X-100, 0.5% sodium deoxycholate 0.1% sodium dodecyl sulphate, 50 mM Tris, pH 8.0). Lysates were centrifuged for 20 min at 15,000 g at 4° C. and supernatants were collected and stored at −80° C. for further analysis. Blood was also collected 6 h after treatment for the assessment of carbon monoxy hemoglobin (HbCO) levels. The release of CO from compounds of the invention was assessed spectrophotometrically by measuring the conversion of deoxyhemoglobin to carbonmonoxy hemoglobin (HbCO). Briefly, fresh mouse blood (0.5 ml) was initially collected in a tube containing 10 µl EDTA (10% solution) as anticoagulant. Using an Hamilton syringe, five microliters of blood were transferred to the bottom of a sealed cuvette containing a small magnetic bar and 4.5 ml of tris(hydroxymethyl)aminomethane solution (20 mM) previously deoxygenated with sodium dithionite. The percent of HbCO was then calculated based on the absorbances at 420 and 432 nm with the reported extinction coefficients for mouse blood. The same method was used to assess the level of HbCO in blood collected from mice 6 h after treatment with compound A or compound B (3 mg) by oral gavage.

Figure 10:
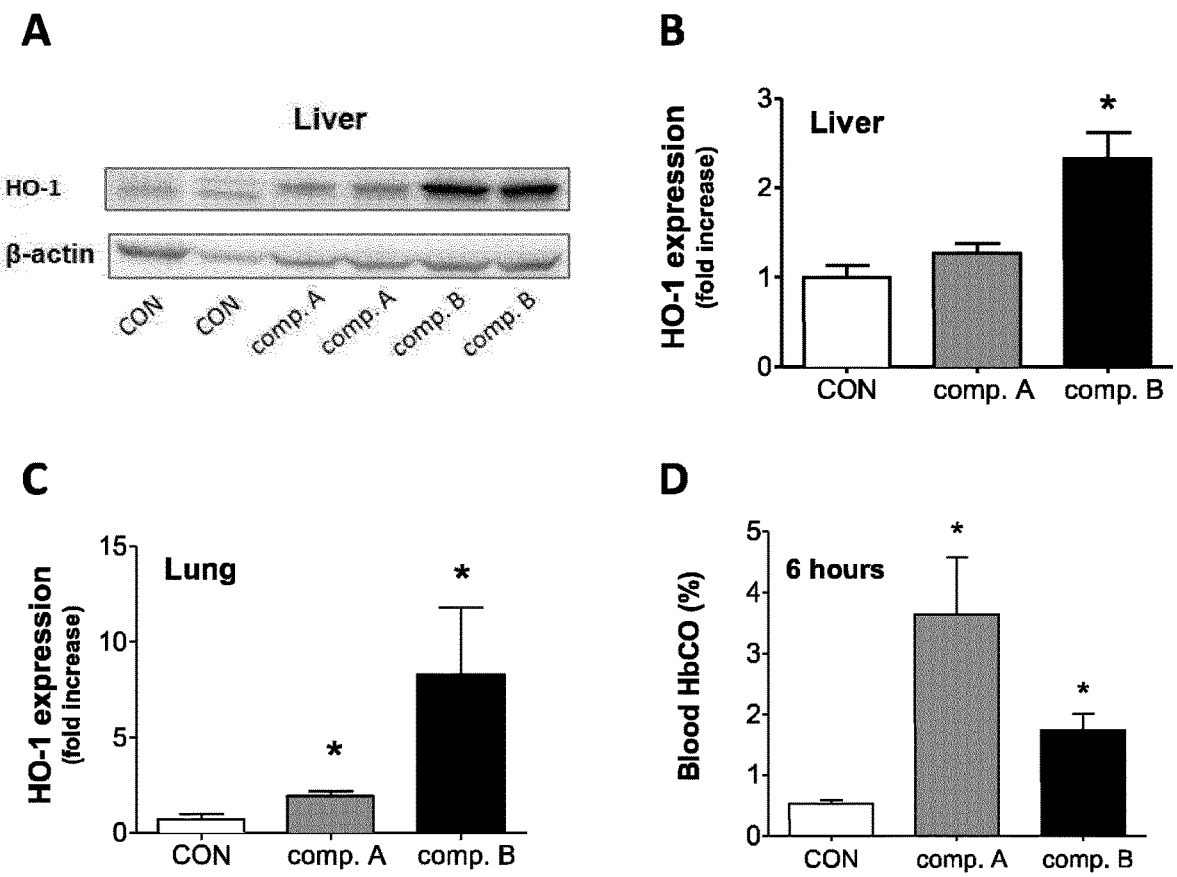
FIG. 10 represents tissue HO-1 expression and blood HbCO levels in vivo after compound A and compound B were administered to mice by oral gavage. (A) Liver and lung HO-1 expression 6 h after oral gavage of mice with compound A and compound B (3 mg in sesame oil). Densitometric analysis of 3 independent Western blots from liver (B) or lung samples (C). (D) Carboxy hemoglobin (HbCO) measured 1 h after treatment of mice with compound A and compound B (n=3 animals).
Figure 11:
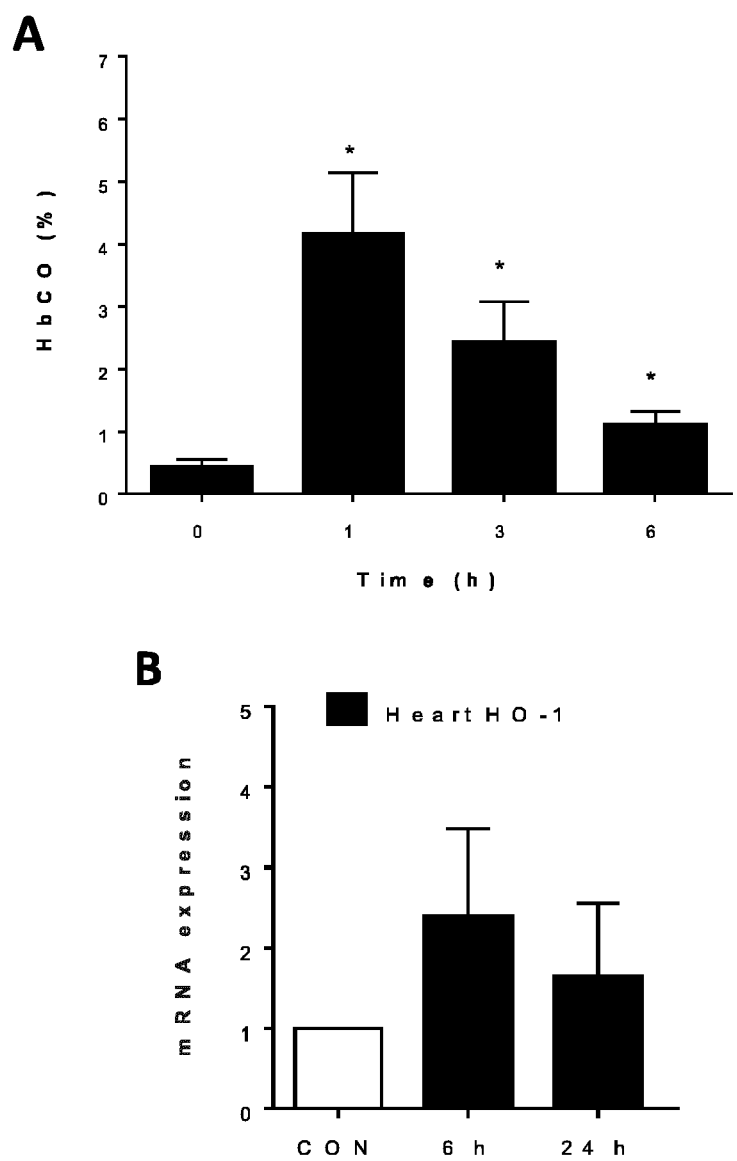
FIG. 11 represents blood HbCO levels in vivo after compound C were administered to mice by oral gavage (FIG. 11A); mRNA expression of Nrf2 dependent genes (HO-1 and NQO-1) in the heart of mice after HbCO after administration of compound C (40 mg/kg) by oral gavage (FIG. 11B).

The results are presented in FIG. 10 and FIG. 11.

Compound B appeared more powerful than compound A in vivo even though the compounds stimulated similar Nrf2 activation and HO-1 expression in BV2 cells.

In parallel to this effect, we measured a consistent elevation of HbCO in blood 6 h after treatment of animals with compounds of the invention (FIG. 10D). Higher levels of HbCO were achieved with compound A compared to compound B, in good accordance with the results obtained in vitro using the hemoglobin assay and the COP-1 probe. Because of this difference and the fact that compound B stimulated higher tissue HO-1 expression than compound A, we presume that the rise in HbCO at 6 h is mostly due to CO released by the $[Co_2(CO)_6]$ moiety of the hybrids and is not yet a reflection of CO derived from heme oxygenase activity.

In addition, compound C promotes an increase in HbCO levels at 1, 3 and 6 hours after administration (FIG. 11A) and compound C promotes an increase in both cardiac HO-1 (6 h) and NQO1 (24 h) in FIG. 11B.

All these experiments demonstrate that compounds of the invention such as compound A, compound B and compound C are potent activators of HO-1 and inducers of HO-1 protein expression via the Nrf2/HO-1 axis at concentrations well below the toxic concentration range. Moreover, comparison of compound C activity with comparative compounds CORM-401 and DMF shows that, at identical concentrations (5 µM), compound C is more potent than DMF and comparative compound CORM-401 at Nrf2 and HO-1 activation.

Thus, inventors discovered two molecules families with the best combined profile (including, CO release, Nrf2 & HO-1 activation, anti-inflammatory potential, GSH modulation, cytotoxicity) and which can be used in in vivo treatments, preferably inflammatory conditions, as they induce tissue HO-1 and deliver CO (i.e. temporary increased in HbCO levels) when administered orally to mice.

The invention claimed is:

1. A compound of the following formula (I):

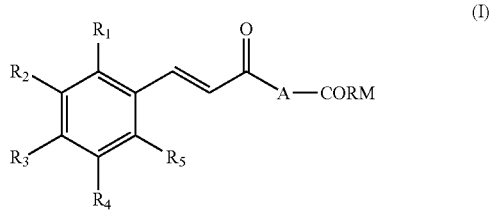

(I)

wherein:
A represents:
  a single bond, or
  -Q-Z—, where:
    Q represents O, S or $NR_6$, wherein $R_6$ represents H, $(C_1-C_6)$alkyl, aryl, heteroaryl, $(C_1-C_6)$alkyl-aryl, $(C_1-C_6)$alkyl-heteroaryl, $(C_1-C_6)$alkyl-$(C_3-C_8)$heterocyclyl, —$(C_3-C_{14})$cycloalkyl, or $R_6$ and Z are connected to form a $(C_3-C_8)$heterocyclyl,
    Z represents —$(C_1-C_6)$alkyl-, —$(C_2-C_6)$alkenyl-, -aryl-, -heteroaryl-, —$(C_2-C_6)$alkynyl-, —$(C_3-C_8)$heterocyclyl-, —$(C_3-C_{14})$cycloalkyl, —$(C_1-C_6)$alkyl-$R_7$—$(C_1-C_6)$alkyl-, —$(C_2-C_6)$alkenyl-$R_7$—$(C_1-C_6)$alkyl-, —$(C_1-C_6)$alkyl-$R_7$—$(C_2-C_6)$alkenyl-, —$(C_2-C_6)$alkenyl-$R_7$—$(C_2-C_6)$alkenyl-, —$(C_1-C_6)$alkyl-$R_7$—$(C_2-C_6)$alkynyl-, —$(C_2-C_6)$alkenyl-$R_7$—$(C_2-C_6)$alkynyl-, —$(C_2-C_6)$alkynyl-$R_7$—$(C_2-C_6)$alkynyl-, —$(C_2-C_6)$alkynyl-$R_7$—$(C_1-C_6)$alkyl-, —$(C_2-C_6)$alkynyl-$R_7$—$(C_2-C_6)$alkenyl-, —$(C_1-C_6)$alkyl-OCO—, or —$CH_2$—$(CHOR_7)CH_2O$—$(C_1-C_6)$alkyl, wherein $R_7$ represents aryl, heteroaryl, $(C_3-C_8)$heterocyclyl, or $(C_3-C_{14})$cycloalkyl, CORM represents a carbonyl metal complex selected from the group consisting of:

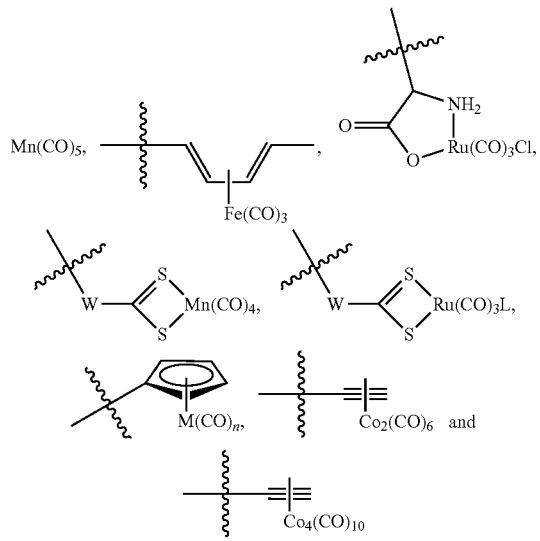

wherein W represents O or $NR_8$, wherein $R_8$ represents $(C_1-C_6)$alkyl,
L represents an ionic ligand, or a counter-ion,
M represents Rh, Co, Ru, Mn, Mo, V or Fe, and
n is an integer chosen so that the metal M has no free valency, and
$R_1$, $R_2$, $R_3$, $R_4$ and $R_5$ represent independently:
  H, —OH, —O$(C_1-C_6)$alkyl, $SO_3H$, $S(C_1-C_6)$alkyl, or $NR_xR_y$, wherein $R_x$ and $R_y$ represent independently H or $(C_1-C_6)$alkyl; or
  two consecutive radicals selected from $R_1$, $R_2$, $R_3$, $R_4$ and $R_5$, taken together, form a bridging group selected from the group consisting of —$(CH_2)_m$—, or —O—$(CH_2)_o$—O—, m being 4 and o being 1 or 2.

2. The compound according to claim 1, wherein $R_1$, $R_2$, $R_3$, $R_4$ and $R_5$ represent independently H, —O$(C_1-C_6)$alkyl or two consecutive radicals selected from $R_1$, $R_2$, $R_3$, $R_4$ and $R_5$, taken together, form a bridging group selected from the group consisting of —O—$(CH_2)_o$—O—, o being 1 or 2.

3. The compound according to claim 1, wherein Q represents O, S or $NR_6$, wherein $R_6$ represents H, $(C_1-C_6)$alkyl and Z represents —$(C_1-C_6)$alkyl-, —$(C_2-C_6)$alkenyl-, —$(C_3-C_8)$heterocyclyl-, —$(C_1-C_6)$alkyl-$R_7$—$(C_1-C_6)$alkyl-, or —$(C_2-C_6)$alkenyl-$R_7$—$(C_1-C_6)$alkyl-, wherein $R_7$ represents heteroaryl or $(C_3-C_8)$heterocyclyl.

4. The compound according to claim 1, wherein CORM represents a carbonyl metal complex selected from the group consisting of:

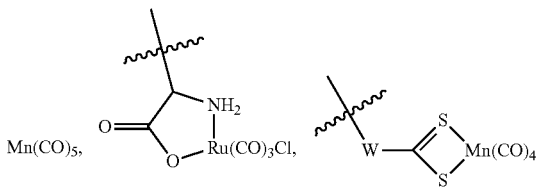

-continued

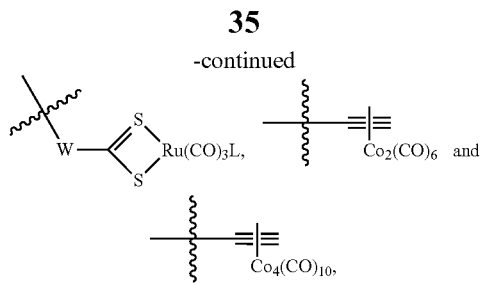

wherein W represents O or NR$_8$, where R$_8$ represents (C$_1$-C$_6$)alkyl, and L represents an ionic ligand or a counter-ion.

5. The compound according to claim 1, selected from the following compounds:

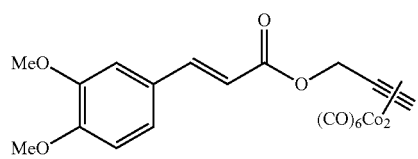

comp. B comp. C

[structure of comp. C]

6. A pharmaceutical composition comprising at least one pharmaceutically acceptable excipient and at least of one compound according to claim 1.

7. The compound of claim 1, wherein L is a halogen, BF$_4$ or PF$_6$.

8. The compound of claim 1, wherein M is Co, Ru or Mn.

9. The compound of claim 3, wherein Q represents O or NR$_6$.

10. The compound of claim 9, wherein R$_6$ represents H or (C$_1$-C$_6$)alkyl.

11. The compound of claim 4, wherein L is a halogen, BF$_4$ or PF$_6$.

12. The pharmaceutical composition of claim 6, wherein L is a halogen, BF$_4$ or PF$_6$.

13. The pharmaceutical composition of claim 6, wherein M is Co, Ru or Mn.

* * * * *